(12) United States Patent
Deisseroth et al.

(10) Patent No.: US 9,458,208 B2
(45) Date of Patent: Oct. 4, 2016

(54) OPTICALLY-BASED STIMULATION OF TARGET CELLS AND MODIFICATIONS THERETO

(71) Applicant: The Board of Trustees of the Leland Stanford Junior University, Palo Alto, CA (US)

(72) Inventors: Karl Deisseroth, Standford, CA (US); Ofer Yizhar, Rehovot (IL); Lisa Gunaydin, San Francisco, CA (US); Peter Hegemann, Falkensee (DE); Andre Berndt, Berlin (DE)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/184,149

(22) Filed: Feb. 19, 2014

(65) Prior Publication Data

US 2014/0235826 A1    Aug. 21, 2014

Related U.S. Application Data

(62) Division of application No. 13/128,979, filed as application No. PCT/US2009/064355 on Nov. 13, 2009, now Pat. No. 8,716,447.

(60) Provisional application No. 61/114,781, filed on Nov. 14, 2008.

(51) Int. Cl.

| | |
|---|---|
| *C07H 21/04* | (2006.01) |
| *C12N 15/00* | (2006.01) |
| *C07K 14/405* | (2006.01) |
| *C07K 14/705* | (2006.01) |
| *A61N 5/06* | (2006.01) |
| *C12N 15/85* | (2006.01) |
| *A01K 67/00* | (2006.01) |
| *A61K 38/00* | (2006.01) |

(52) U.S. Cl.
CPC .......... *C07K 14/405* (2013.01); *A61N 5/062* (2013.01); *C07K 14/705* (2013.01); *C12N 15/85* (2013.01); *A61K 38/00* (2013.01)

(58) Field of Classification Search
CPC ... C07K 14/405; C07K 14/705; C12N 15/85
USPC .................. 530/370; 536/23.6; 435/320.1
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Ionis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,290,280 A | 3/1994 | Daikuzono, et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray, et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |

(Continued)

FOREIGN PATENT DOCUMENTS

| | | |
|---|---|---|
| CN | 1079464 A | 12/1993 |
| EP | 1334748 | 8/2003 |

(Continued)

OTHER PUBLICATIONS

Cazillis et al., "VIP and PACAP induce selective neuronal differentiation of mouse embryonic stem cells", Eur J Neurosci, 2004. 19(4):798-808.

Morelli et al., "Neuronal and glial cell type-specific promoters within adenvirus recombinants restrict the expression of the apoptosis-inducing molecule Fas ligand to predetermined brain cell types, and abolish peripheral liver toxicity", Journal of General Virology, 1999, 80:571-583.

Berke, et al. "Addiction, Dopamine, and the Molecular Mechanisms of Memory", Molecular Plasticity, 2000, vol. 25: pp. 515-532.

Goshen et al. "Dynamics of Retrieval Strategies for Remote Memories", Cell, 2011, vol. 147: pp. 678-589.

Jimenez S.A. & Maren S. et al/ "Nuclear disconnection within the amygdala reveals a direct pathway to fear", Learning Memory, 2009, vol. 16: pp. 766-768.

(Continued)

*Primary Examiner* — Quang Nguyen

(74) *Attorney, Agent, or Firm* — Bozicevic, Field & Francis LLP; Paula A. Borden

(57) ABSTRACT

Stimulation of target cells using light, e.g., in vivo or in vitro, is implemented using a variety of methods and devices. One example involves a vector for delivering a light-activated molecule comprising a nucleic acid sequence that codes for light-activated molecule. The light-activated molecule includes a modification to a location near the all-trans retinal Schiff base, e.g., to extends the duration time of the open state. Other aspects and embodiments are directed to systems, methods, kits, compositions of matter and molecules for ion channels or pumps or for controlling currents in a cell (e.g., in in vivo and in vitro environments).

11 Claims, 10 Drawing Sheets

(56) References Cited

U.S. PATENT DOCUMENTS

| | | |
|---|---|---|
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,057,114 A | 5/2000 | Akong |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller, et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,815,582 B2 * | 8/2014 | Deisseroth et al. ......... 435/325 |
| 8,906,360 B2 | 12/2014 | Deisseroth et al. |
| 8,926,959 B2 | 1/2015 | Deisseroth et al. |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0068202 A1 | 4/2004 | Hansson et al. |
| 2004/0073278 A1 | 4/2004 | Pachys |
| 2004/0076613 A1 | 4/2004 | Mazarakis et al. |
| 2004/0122475 A1 | 6/2004 | Myrick et al. |
| 2004/0203152 A1 | 10/2004 | Calos |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | de Charms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |

(56) References Cited

U.S. PATENT DOCUMENTS

| | | |
|---|---|---|
| 2008/0077200 A1 | 3/2008 | Bendett et al. |
| 2008/0085265 A1 | 4/2008 | Schneider et al. |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0234273 A1 | 9/2010 | Deisseroth et al. |
| 2011/0021270 A1 | 1/2011 | Vo-Dinh et al. |
| 2011/0092800 A1 | 4/2011 | Yoo et al. |
| 2011/0105998 A1 | 5/2011 | Zhang et al. |
| 2011/0112179 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Deisseroth et al. |
| 2011/0172653 A1 | 7/2011 | Deisseroth et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0165904 A1 | 6/2012 | Deisseroth et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0089503 A1 | 4/2013 | Deisseroth et al. |
| 2013/0090454 A1 | 4/2013 | Deisseroth et al. |
| 2013/0144359 A1 | 6/2013 | Kishawi et al. |
| 2013/0184817 A1 | 7/2013 | Deisseroth et al. |
| 2013/0224821 A1 | 8/2013 | Deisseroth et al. |
| 2013/0244323 A1 | 9/2013 | Deisseroth et al. |
| 2013/0284920 A1 | 10/2013 | Deisseroth et al. |
| 2013/0288365 A1 | 10/2013 | Deisseroth et al. |
| 2013/0289386 A1 | 10/2013 | Deisseroth et al. |
| 2013/0289669 A1 | 10/2013 | Deisseroth et al. |
| 2013/0289675 A1 | 10/2013 | Deisseroth et al. |
| 2013/0289676 A1 | 10/2013 | Deisseroth et al. |
| 2013/0295015 A1 | 11/2013 | Deisseroth et al. |
| 2013/0295635 A1 | 11/2013 | Deisseroth et al. |
| 2013/0296406 A1 | 11/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0331441 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0024701 A1 | 1/2014 | Deisseroth et al. |
| 2014/0082758 A1 | 3/2014 | Deisseroth et al. |
| 2015/0112411 A1 | 4/2015 | Beckman et al. |

FOREIGN PATENT DOCUMENTS

| | | |
|---|---|---|
| EP | 1873566 | 1/2008 |
| JP | 2006-295350 | 10/1994 |
| JP | 2010227537 A | 10/2010 |
| WO | WO 96/32076 | 10/1996 |
| WO | WO 00/27293 | 5/2000 |
| WO | WO 01/25466 | 4/2001 |
| WO | WO 03/016486 | 2/2003 |
| WO | WO 2013/016486 | 2/2003 |
| WO | WO 03/040323 | 5/2003 |
| WO | WO 03/084994 | 10/2003 |
| WO | WO 03/102156 | 12/2003 |
| WO | WO 2004/033647 | 4/2004 |
| WO | WO 2007/024391 | 3/2007 |
| WO | WO 2007/131180 | 11/2007 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | 2009-0131837 | 10/2009 |
| WO | WO 2009/119782 | 10/2009 |
| WO | WO 2009/131837 | 10/2009 |
| WO | WO 2010/006049 | 1/2010 |
| WO | WO 2010/011404 | 1/2010 |
| WO | WO 2010/056970 | 5/2010 |
| WO | WO-2010123993 | 10/2010 |
| WO | WO 2011/005978 | 1/2011 |
| WO | WO 2011/066320 | 6/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 | 10/2012 |
| WO | WO 2013/126521 | 8/2013 |
| WO | WO 2013/142196 | 9/2013 |

OTHER PUBLICATIONS

Ehrlich I. et al. "Amygala inhibitory circuits and the control of fear memory", Neuron, 2009. Friedrich Meischer Institute, vol. 62: pp. 757-771.

Berndt et al. "Bi-stable neural state switches", Nature Neuroscience, 2009, vol. 12, No. 2: pp.229-234.

Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.

Gradinaru et al., "Targeting and readout strategies for fast optical neural control in vitro and in vivo", J Neuroscience, 2007, 27(52):14231-14238.

Davis; "The many faces of epidermal growth factor repeats," The New Biologist; vol. 2, No. 5, pp. 410-419 (1990).

De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).

EBI accession No. UNIPROT: A7U0Y6; "SubName: Full=Bacteriorhodopsin", (Aug. 10, 2010).

Ihara, et al.; "Evolution of Archaeal Rhodopsins: Evolution Rate Changes by Gene Duplication and Functional Differentiation"; J. Mol. Biol.; vol. 285, pp. 163-174 (1999).

Kaiser; "Clinical research. Death prompts a review of gene therapy vector"; Science; 317(5838):580 (Aug. 3, 2007).

Kay; "State-of-the-art gene-bases therapies: the road ahead"; Nature Reviews Genetics; vol. 12, pp. 316-328 (May 2011).

(56) References Cited

OTHER PUBLICATIONS

Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.
Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential for use in research and the clinic", Brain stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.
Peralvarez-Marin et al., "Inter-helical hydrogen bons are essential elements for intra-protein signal transduction: The role of Asp115 in bacteriorhodopsin transport function", J. Mol. Biol., 2007, vol. 368, pp. 666-676.
Pinkham et al., "Neural bases for impaired social cognition in schizophrenia and autism spectrum disorders", Schizophrenia Research, 2008, vol. 99, pp. 164-175.
Sohal et al., "Parvalbumin neurons and gamma rhythms enhace cortical circuit performance", Nature, 2009, vol. 459, No. 7247, pp. 698-702.
Yizhar et al., "Optogenetics in neural systems", Neuron Primer, 2011, vol. 71, No. 1, pp. 9-34.
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Express from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Cowan et al., "Targeting gene expression to endothelium in transgenic animals: a comparison of human ICAM-2, PECAM-1, and endoglin promotoers", Xenotransplantation, 2003, vol. 10, pp. 223-231
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. And Biol., 2001, vol. 501, pp. 269-278.
Mullins et al., "Fulminant hypertension in transgenic rats harbouring the mouse *Ren-2* gene", Nature, 1990, vol. 344, pp. 541-544.
Mullins et al., "Expression of the DBA/2J *Ren-2* gene in the adrenal gland of transgenic mice", EMBO, 1989, vol. 8, pp. 4065-4072.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Adamantidis, et al., "Optogenetic Interrogation of Dopaminergic Modulation of Multiple Phases of Reward-Seeking Behavior", J. Neurosci, 2011, vol. 31, No. 30, pp. 10829-35.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila* rhodopsin cytoplasmic tail domain is required for maintenance of rhabdomere structure." The FASEB Journal, 2007, vol. 21, p. 449-455.
Airan, et al., "Temporally Precise in vivo Control of Intracellular Signaling", 2009, Nature, vol. 458. No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ang, et al. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the *cre* Gene Mediated by Cre Recombinase Using a Combination of Mutant *lox* Sites", Nucleic Acids Research, 2002, vol. 30, No. 19, pp. 1-8.
Aravanis, et al, "An optical neural interface: in vivo control of rodent motor cortex with integrated fiberoptic and optogenetic technology," J. Neural. Eng., 2007, vol. 4(3):S143-S156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin,"Proc. Natl. Academy Science USA, 1993, vol. 90, No. 2, p. 639-643.
Banghart, et al. "Light-activated ion channels for remote control neuronal firing", Nature Neuroscience. 2004, vol. 7, No. 12 pp. 1381-1386.
Basil et al. "Is There Evidence for Effectiveness of Transcranial Magnetic Stimulation in the Treatment of Psychiatric Disorders?" Psychiatry, 2005, pp. 64-69.
Bebbington et al. "The use of vectors based on gene amplification for the expression of cloned genes in mammalian cells in DNA cloning" vol. 3, Academic Press, New York, 1987.
Benabid "Future strategies to restore brain functions." Conference proceedings from the Medicine Meets Millennium: World Congress of Medicine and Health. 2000, 6 pages.
Benoist et al. "In vivo sequence requirements of the SV40 early promotor region" Nature (London). 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.

(56) References Cited

OTHER PUBLICATIONS

Bocquet et al. "A prokaryotic proton-gated ion channel from the nicotinic acetylcholine receptor family." Nature Letters, 2007, vol. 445, p. 116-119.
Boyden, et al. "Millisecond-timescale, genetically targeting optical control of neural activity" Nature Neuroscience, 2005, vol. 8. No. 9: pp. 1263-1268.
BL et al. "Ectopic Expression of a Microbial-Type Rhodopsin Restores Visual Responses in Mice with Photoreceptor Degeneration", Neuron, 2006, vol. 50, No. 1: pp. 23-33.
BL et al. "Synaptic Modifications in Cultured Hippocampal Neurons: Dependence on Spike Timing, Synaptic Strength, and Postsynatic Cell Type", Journal of Neuroscience, 1998, vol. 18. No. 24: pp. 10464-10472.
Basil et al. "Is There Evidence for Effectiveness of Transcranial Magnetic Stimulation in the Treatment of Psychiatric Disorders?" Psychiatry, 2006, pp. 64-69.
Blomer et al., "Highly Efficient and Sustained Gene Transfer in Adult Neurons with Lentivirus Vector", Journal of Virology,1997, vol. 71, No.9: pp. 6641-6649.
Braun. "Two Light-activated Conductances in the Eye of the Green Alga Volvox carteri", 1999, Biophys J., vol. 76, No. 3, pp. 1668-78.
Brinton, et al. "Preclincial analyses of the therapeutic potential of allopregnanolone to promost neurogenesis in vitro and invivo in transgenic mouse model of Alzheimer's disease." Current Alzheimer Research, 2006, vol. 3. No. 1: pp. 11-7.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by 0 frequency stimulation is regulated by a protein phosphate-operated gate," The Journal of Neuroscience, 2000, vol. 20, No. 21, pp. 7880-7887.
Callaway, et al. "Photostimulation using caged glutamate reveals functional circuitry in living brain slices", Proc. Natl. Acad. Sci. USA., 1993, vol. 90: pp. 7661-7665.
Campagnola et al, "Fiber coupled light-emitting diode for localized photostimulation of neurons exoressing channelrhodopsin-2," Journal of Neuroscience Methods , 2008, vol. 169, Issue 1. Abstract only.
Cardin, et al. "Driving Fast spiking Cells induces Gamma Rhythm and Controls Sensory Responses", 2009, Nature, vol. 459, vol. 7247, pp. 663-667.
Cenatiempo "Prokaryotic gene expression in vitro: transcription-translation coupled systems", Biochimic, 1986, vol. 68(4): pp. 505-515.
Claudio et al. "Nucleotide and deduced amino acid sequences of Torpedo californica acetylcholine receptor gamma subunit, "PNAS USA,1983, vol. 80. p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of Medial Prefrontal Cortex." Journal of Neuroscience, 2010, vol. 30(48), pp. 16082-16090.
Crouse, et al. "Expression and amplication of engineered mouse dihydrofolate reductase minigenes" Mol. Cell. Biol., 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microse. Tech., 1990, 15 (4):352-368.
Cucchiaro et al., "Electron-Microfot Analysis of Synaptic Input from the Perigeniculate Nucleus to A-Lamine of the Lateral Geniculate Nucleus in Cats", The Journal of Comparitive Neurology, 1991, vol. 310, pp. 316-336.
Cul et al., "Electrochemical deposition and characterization of conducting polymer polypyrrole/PSS on multichannel neural probes," Sensors and Acuators, 2001, vol. 93(1): pp. 8-18.

Date, et al, "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994, vol. 265, pp. 255-258.
Dederen, et al, "Retrograde neuronal tracing with cholera toxin B subunit: comparison of three different visualization methods", Histochemical Journal, 1994, vol. 26, pp. 856-862.
De Foubert et al. "Fluoxetine-Induced Change in Rat Brain Expression of Brain-Derived Neurotrophic Factor Varies Depending On Length and Treatment," Neuroscience, 2004, vol. 128, pp. 597-604.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechaniams", Current Opinion in Neurobiology, 2003, vol. 13, pp. 354-65.
Deisseroth et al., "Excitation-neurogenesis Coupling in Adult Neural Stem/Progenitory Cells", 2004, Neuron, vol. 42, pp. 535-552.
Deisseroth "Next-generation optical technologies for illuminating genetically targeting brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachines from silicon-on-insulator wafer," Med. Biol. Eng. Comput., 2000, vol. 38, pp. 175-179.
Eisen, "Treatment of amyotrophic laterl sclerosis", Drugs Aging, 1999; vol. 14, No. 3, pp. 173-96.
Ernst, et al. "Photoactivation of Channelrhodopsin", 2008, J. Biol. Chem. vol. 283, No.3, pp. 1637-1643.
Evanko "Optical excitation yin and yang" Nature Methods, 2007, 4:384.
Espositio et al. "The integrase family of tyrosine recombinases: evolution of a conserved active site domain", Nucleic Acids Research. 1997. vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening. 2002. vol. 7, No. 5, pp. 460-465.
Farber, et al. "Indentification of presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neueon, 2000, Vol. 28, pp. 41-51.
Fisher, J. et al. "Spatiotemporal Activity Patterns During Respiratory Rhythmogenesis in the Rat Ventrolatera; Medulla." The Journal of Neurophysiol, 2006, vol. 95, pp. 1982-1991.
Fitzsimmons et al., "Promotoers and Regulatory Elements the Improve Adeno-Associated Virus Transgene Expression in the Brain", 2002, Methods, vol. 28, pp. 227-236.
Foster. "Bright blue times", Nature, 2005, vol. 433, pp. 698-699.
Gelvich et al. "Contact flexible microstrip applicators (CFMA) in a range from microwaves up to short waves," IEEE Transactions on Biomedical Engineering, 2002, vol. 49, Issue 9: 1015-1023.

(56) References Cited

OTHER PUBLICATIONS

Gigg, et al. "Glutamateric hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al. "Factors affecting the expression of foreign proteins in *Escherichia coli* ", Journal of Industrial Microbiology, 1987, vol. 1(5): pp. 277-282.
Goekoop, R. et al. "Cholinergic challenge in Alzheimer patients and mild cognitive impairment differentially affects hipppocampal activation-a pharmacological fMRI study." Brain. 2006, vol. 129, pp. 141-157.
Gold, et al. "Representation of a perceptual decision in developing oculomotor commands", Nature, 2000, vol. 404, pp. 390-394.
Gonzalez, et al., "Cell-based Assays and Instrumentation for Screeming Ion-Channels Targets", DDT, 1999, vol. 4, No. 9, pp. 431439.
Gordon, et al. "Regulation of Thy- 1 Gene Expression in Transgenic Mice", Cell, 1987, vol. 50. pp. 445-452.
Gorelova et al., "The course of neural projection from the prefrontal cortex to the nucleus accumbens in the rat", Neuroscience, 1997, vol. 76, No. 3, pp. 689-706.
Gottesman et al. "Bacterial regulation: global regulatory networks. "Ann. Rev. Genet. , 1984, vol. 18, pp. 415-441.
Gradinaru, et al. "ENpHR: a Natronomonas Halorhodopsin Enhanced for Optogentic Applications", 2008, Brain Cell Biol., vol. 36 (1-4), pp. 129-139.
Gradinaru, et al., Molecular and Cellular Approaches for Diversifying and Extending Optpgenetics, Cell, 2010, vol. 141, No. 1, pp. 154-165.
Greenburg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage ϕBT1 and development of site-specific integrated vectors", Journal of Bacteriology, 2003. vol. 185, No. 17, pp. 5320-5323.
Groth et al. "Phage integrases: biology and applications." Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of doparninergic neurons of the substantia nigra pars compacta: Involvement of transient receptor potential channels,"Journal of Neurophysiol. , 2005. vol. 94, pp. 3069-3080.
Gulick, et al. "Transfection using DEAE-Dextran" Supplement 40. Current Protocols in Molecular Biology, 1997, Supplement 40, 9.2.1-9.2.10.
Gur et al., "A dissociation Between Brain Acticity and Perception: Chromatgically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genentic rearrangements," FEMS Microbiology Reviews, 1997, vol. 21, No. 2, pp. 157-178.
Hamer, et al. "Regulatin *In Vivo* of a cloned mammalian gene: cadmium induces the transcription of a mouse metallothionein gene in SV40 vectors," Journal of Molecular Applied Genetics, 1982, vol. 1, No. 4, pp. 273-288.
Han, et al., "Multiple-Color Optical Activation, Silencing, and Desynchronization of Neural Activity with Single-Spike Temporal Resoluation", PLoS One, 2007, vol. 2, No. 3, pp. 1-12.
Hausser, et al. "Tonic Synaptic Inhibition Modulates Neuronal Output Pattern and Spatiotemporal Synaptic Integration", Neuron, 1997, vol. 19, pp. 665-678.

Hegemann et al., "All-trans Retinal Constitutes the Functional Chromophore in *Chlamydomonas* rhodopsin", Biophys. J., 1991. vol. 60. pp. 1477-1489.
Herlitze, et al., "New Optical Tools for Controlling Neuronal Activity", 2007, Curr Opin Neurobiol, vol. 17. No. 1. pp. 87-94.
Herry, et al. "Switching on and off fear by distinct neuronal circuits," Nature, 2008, Vol. 454, pp. 600-606.
Hikida et al., "Increased sensitivity to cocaine by cholingeric cell ablation in nucleus accumbens," PNAS, Nov. 2001, 98(23):13351-13354.
Hikida et al., "Acetlycholine enchancement in the nucleus accumbens prevents addictive behaviors of cocaine and morphine", PNAS, May 2003, 100(10):6169-6173.
Hildebrandt et al, "Bacteriorhodopsin expressed in *Schizosaccharomyces pombe* pumps protons through the plasma membrane," PNAS, 1993, vol. 90, pp. 3578-3582.
Hirase, et al. "Multiphoto stimulation of neurons", J Neurobiol, 2002, vol. 51, No. 3: pp. 237-47.
Hodaie, et al., "Chronic Anterior Thalamus Stimulation for Intractable Epilepsy," Epilepsia, 2002. vol. 43, pp. 603-608.
Hoffman et al., "K+ Channel Regulation of Signal Propagation in Dendrites of Hippocampal Pyramidal Neurons", 1997, Nature. vol. 387: pp. 869-874.
Hofherr et al. "Selective Golgi export of Kir2.1 controls the stoichiometry of functional Kir2.x channel heteromers"Journal of Cell Science, 2005, vol. 118. p. 1935-1943.
Hosokawa, T. et al. "Imaging spatio-temporal patterns of long-term potentiation in mouse hippocampus," Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
Isenberg et al. "Cloning of a Putative Neuronal Nicotinic Aceylcholine Receptor Subunit," Journal of Neurochemistry. 1989. pp. 988-991.
Jekely, "Evolution of Phtoaxis", 2009, Phil. Trans. R. Soc. B, vol. 364. pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene *GAL4* and analysis of its dosage effects on the galactose/meliboise regulon," PNAS, 1982, vol. 79. pp. 6971-6975.
Kandel, E.R.,et al. "Electrophysiology of Hippocampal Neurons: I. Sequential Invasion and Synaptic Organization." J Neurophysiol. 1961, vol. 24, pp. 225-242.
Kandel, E.R.,etal. "Electrophysiology of Hippocampal Neurons: II. After-Potentials and Repetitive Firing", J Neurophysiol., 1961, vol. 24. pp. 243-259.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia," Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods. 1994. vol. 54. pp. 205-218.
Khodakaramian, et al. "Espression of Cre Recombinase during Transient Phage Infection Permits Efficient Marker Removal in *Streptomyces*," Nucleic Acids Research, 2006, vol. 34, No. 3:e20. pp. 1-5.
Khossravani et al., "Voltage-Gated Calcium Channels and Idiopathic Generalized Epilepsies", Physiol. Rev., 2006. vol. 86: pp. 941-966.
Kianianmomeni, et al. "Channelrhodopsins of Volvox carteri are Photochromic Proteins that are Specifically Expressed in Somatic cells under Control of Light, Temperature, and the Sex Inducer", 2009, Plant Physiology, vol 151, No. 1, pp. 347-366.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.

(56) References Cited

OTHER PUBLICATIONS

Kingston et al. "Transfection of DNA into Eukaryotic Cells,"Supplement 63. Current Protocols in Molecular Biology. 1996, 9.1.1-9.1.11, 11 pages.
Kingston et al. "Transfection and Expression of Cloned DNA," Supplement 31, Current Protocols in Immunology, 1999, 10.13.1-10.13.9.
Kinoshita, et al., "Optogenetically Induced Supression of Neural Activity in the Macaque Motor Cortex", Poster Sessions Somatomotor System, Others.2010, pp. 141-154.
Kita, H. et al. "Effects of dopamine agonists and antagonists on optical responses evoked in rat frontal cortex slice after stimulation of the subcortical white matter," Exp. Brain Research. 1999, vol. 125, pp. 383-388.
Kitabatake et al., "Impairment of reward-related learning by cholinergie cell ablationn in the striatum", PNAS. Jun. 2003, 100(13):7965-7970.
Kitayama, et al "Regulation of neuronal differentiation by N-menthyk-D-aspartate receptors expressed in neural progenitor cells isolated from adult mouse hippocampus," Journal of Neurosci Research, 2004. vol. 76. No. 5: pp. 599-612.
Klausberger, et al. "Brain-state- and cell-type-specific firing of hippocampal interneurons *in vivo*", Nature, 2003. vol. 421: pp. 844-848.
Kocsis et al., "Regenerating Mammalian Nerve Fibres: Changes in Action Potential Wavefrom and Firing Characteristics Following Blockage of Potassium Conductance", 1982. Proc. R. Soc. Lond., vol. B 217: pp. 77-87.
Knopfel, et al. "Optical Probin of Neuronal Circuit Dynamics: Gentically Encoded Versus Classical Fluorescent Sensor", 2006, Trends Neurosci, vol. 29, No. 3, pp. 160-166.
Kuhlman et al. (2008) "High-Resolution Labeling and Functional Manipulation of Specific Neuron Types in Mouse Brain by Cre-Activated Viral Gene Expression" PLoS One, 2005, vol. 3. No. 4, pp. 1-11.
Kumkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Lanyi et al. "The primary structure of a Halorhodopsin from Natronobacterium Pharaonis" Journal of Biological Chemistry, 1990, vol. 265, No. 3, p. 1253-1260.
Landy, A. "Mechanistic and structural complexity in the site-specific recombination pathways of Int and FLP", Current Opinion in Genetics and Development, 1993. vol. 3. pp. 699-707.
Lee et al, "Sterotactic Injection of Adenviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gone Therapy Can Prevent Neuron Deatch Resulting from Necrotic and Apoptotic Insults", Journal of Neurochemistry, 2003. vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al, "Fast noninvasive activation and inhibition of neural and network activity by vertebrate rhodopsin and green algae channelrhodopsin," PNAS, 2005, vol. 102, No. 49, p. 17816-17821.
Lim et al., "A Novel Targeting Signal for Proximal Clustering of the Kv21K+ Channel in Hippocampal Neurons", Neuron. 2000. vol. 25: pp. 385-397.
Lima, et al. "Remote Control of Behavior through Genetically Targeted Photstimulation of Neurons", Cell. 2005, vol. 121: pp. 141-152.
Liman, et al. "Subunit Stoichiometry of Mammalian K+ Channel Determined by Construction of Multimeric cDNAs," Neuron, 1992, vol. 9, pp. 861-971.
Louis et al. "Cloning and sequencing of cellular-viral junctions from the human adenovirus type 5 transformed 293 cell line," Virology, 1997. vol. 233, pp. 423-429.

Loetterle, et al., "Cerebellar Stimulation: Pacing the Brain". American Journal of Nursing, 1975, vol. 75, No. 6, pp. 958-960.
Luecke, et al. "Structual Changes in Bacteriorhodopsin During Ion Transport at 2 Angstrom Resolution," Science. 1999, vol. 286, pp. 255-260.
Lyznik, et al. "FLP-mediated recombination of *FRT* sites in the maize genome," Nucleic Acids Research , 1996. vol 24, No. 19: pp. 3784-3789.
Ma et al. "Role of ER Export Signals in Controlling Surface Potassium Channel Numbers," Science. 2001. vol. 291, pp. 316-319.
Marin, et al., The Amino Terminus of the Fourth Cytoplasmic Loop Rhodopsin Modulates Rhodopsin-Transduction Interaction. The Journal of Biological Chemistry. 2000. vol. 275, pp. 1930-1936.
Mann et at. "Perisomatic Feedback Inhibtion Underlies Cholinergically Induced Fast Network Oscillations in the Rat Hippocampus in Vitro," Neuron, 2005, vol. 45, 2005, pp. 105-117.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell. 1982, vol. 31 pp. 355-365.
Melyan, Z. et al. "Addition of human melanopsin renders mammalian cells Photoresponsive", Nature. 2005. vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials". The Journal of Neuroscience, 2000, vol. 20, No. 1, pp. 266-273.
Meyer, et al. "High density interconnects and flexible hybrid assemblies for active biomedical implants," IEEE transactions on Advanced Packaging , 2001. vol. 24, No. 3, pp. 366-372.
Milella et al. "Opposite roles of dopemine and orexin in quinpirole-induced excessive drinking: a rat model of psychotic polydipsia" Psychopharmacology, 2010, 211:355-366.
Monje et al., "Irradiation Induces Neural Precursor-Cell Dusfunction", Natural Medicine, 2002, vol. 8, No. 9, pp. 955-962.
Mortensen et al. "Selection of Transfected Mammalian Cells," Supplement 86, Current Protocols in Molecular Biology, 1997, 9.5.1-09.5.19.
Nacher, et al. "NMDA Receptor antagonist treatment increases the production of newneurons in the aged rat hippocampus", Neurobiology of Aging, 2003, vol. 24, No. 2: pp. 273-84.
Nagel et al. "Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al, "Channelrhodopsin-I: a light-gated proton channel in green algae". Science, 2002, vol. 296: pp. 2395-2398.
Nagel, et al, "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al, "Damage to the insula disrupts addiction in cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006. vol. 46. No. 27: pp. 4575-81.
Nirenberg, et al. "The Light response of Retinal Ganglion Cells is Truncated by a Displaced Amacrine Circuit", Neuron, 1997, vol. 18: pp. 637-650.
Nunes-Duby, et al. "Similarities and differences amoung 105 members of the Int family of site-specific recombinases", Nucleic Acids Research. 1998, vol 26, No. 2: pp. 391-406.
O'Gorman et al. "Recombinase-mediated gene activation and site-specific integration in mammalian cells", Science, 1991, 251(4999): pp. 1351-1355.

(56) References Cited

OTHER PUBLICATIONS

Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neutral Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al, "Functional Expression of Directly Light-Gated Membrane Channel in Mammalian Retinal Neurons: A Potential Strategy for Restoring Light Sensitivity to Retina After Photoreceptor Degeneration,"Investigative Opthalmology & Visual Science, 2005, 46 E-Abstract 4631. Abstract only.
Panda, et al. "Illumination of the Melanopsin Signaling Pathway", Science, 2005. vol. 307: pp. 600-604.
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kit1) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68. Current Protocols in Molecular Biolog, 1996. 9.11.1-9.11.18.
Peterlin, et al. "Optical probing of neuronal circuits with calcium indicators," PNAS, 2000, vol. 97, No. 7: pp. 3619-3624.
Petersen et al, "Spatiotemporal Dynamics of Sensory Responses in Layer 2/3 of Rat Barrel Cortex Measured *In Vivo* by Voltage-Sensitive Dye Imaging Combined with Whole-Cell Voltage Recordings and Neuron Reconstructions." The Journal Neuroscience, 2003, vol. 23. No. 3, pp. 1298-1309.
Petrecca, et al. "Localization and Enhanced Current Density of the Kv4.2 Potassium Channel by Interaction with the Actin-Binding Protein Filamin," The Journal of Neuroscience. 2000. vol. 20. No. 23. p. 8736-8744.
Petit, et al. "Local Excitatory Circuits in the Intermediate Gray Layer of the Superior Colliculus", J Neurophysiol., 1999. vol. 81, No. 3: pp. 1424-1427.
Potter, "Transfection by Electroportation." Supplement 62. Current Protocols in Molecular Biology, 1996, 9.3.1-9.6.3.
Pouille, et al. "Routing of spike series by dynamic circuits in the hippocampus", Nature, 2004, vol. 429: pp. 717-723.
Qiu et al. "Induction of photosensitivity by hererologous expression of melanopsin", Nature, 2005, vol. 433: pp. 745-749.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, Vol. 12, No. 7, pp. 2534-46.
Randic, et al. "Long-term Potentiation and Long-term Depression of Primary Afferent Neurotransmission in the Rat Spinal Cord", 1993, Journal of Neuroscience, vol. 13, No. 12, pp. 5228-41.
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopemine and Noradrenaline Innervation in the Limbic System", Brain, 2005. vol. 128 (Pt 6), pp. 1314-1322.
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50. pp. 35033-35041.
Rivera et al., "BDNF-Induced TrkB Activation Down-Regulates the K+-Cl- cotransporter KCC2 and Impairs Neuronal Cl- Extrusion", The Journal of Cell Biology, 2002. Vol. 159: pp. 747-752.
Rosenkranz, et al, "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polymide-based intracortical electrode arrays with bioactive capability,"IEEE Transactions on the Biomedical Engineering, 2001. vol. 48. No. 3, pp. 361-371.
Rubinson et at. "A lentivirus-based system to functionally silence genes in primary mammalian cells, stem cells and transgenic mice by RNA interference," Nature Genetics, 2003. vol. 33. p. 401-406.
Rudiger et at, "Specific arginine threonin residues control anion binding and transport in the light-driven chloride pump halorhodopsin," The EMBO Journal, 1997, vol. 16, No. 13, pp. 3813-3821.
Salzman, et al. "Cortical microstimulation influences and perceptual judgements of motion direction", Nature, 1990. vol. 346, pp. 174-177.
Saidyk, et al., "Excitatory Amino Acid Receptors in the Basolateral Amygdala Regulate Anxiety Responses in the Social Interation Test" , Brain Research. 1997, vol. 764. pp. 262-264.
Sato et al, "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994. vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008. vol. 33, pp. 368-377.
Sclimenti, et al. "Directed evolution of a recombinase for improved genomic integration at a native human sequence," Nucleic Acids Research, 2001, vol. 29. No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience. 2007. vol. 27, No. 7: pp. 1566-1575.
Silver, et al. "Amino terminus of yeast *GAL4* gene product is sufficient for nuclear localization" PNAS, 1984. vol. 81, No. 19: pp. 5951-5955.
Singer et al. "Elevated Intrasynaptic Dopamine Release in Tourette's Syndrome Measured by PET." American Journal of Psychiatry. 2002. vol. 159: pp.1329-1336.
Slimko et al., "Selective Electrical Silencing of Mammalian Neurons *In Vitro* by the use of Invertabrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Song et al. "Differential Effect of TEA on Long-Term Synaptic Modification in Hippocampal CA1 and Dentate Gyrus *in vitro* ." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Stark, et al. "Catalysis by site-specific recombinases," Trends Genet., 1992. vol. 8, No. 12: pp. 432-439.
Stockklausner et al. "A sequence motif responsible for ER export and surface expression of Kir2.0 inward rectifier K+ channels," FEBS Letters. 2001, vol. 493, pp. 129-133.
Stoll, et al. "Phage TP901-I site-specific integrase functions in human cells," Journal of Bacteriology, 2002. vol. 184, No. 13: pp. 3657-3663.

(56) References Cited

OTHER PUBLICATIONS

Swanson, "Lights, Opsins, Action! Optogenetics Brings Complex Neuronal Circuits into Sharper focus", 2009, The Dana Foundation, [URL: http://www.dana.org/news/features/detail.aspx?id=24236], PDF File. pp. 1-3.
Swiss-Prot_Q2QCJ4, Opsin 1, Oct. 31, 2006, URL:http://www.ncnbi.nlm.nig.gov/protein/Q2QCJ4.
Tamai, "Progress in Pathogenesis and Therapeutic Research in Retinitis Pigmentosa and Age Related Macular Degeneration", NIPPON GANKA GAKKAI ZASSHI, vol. 108. No. 12, Dec. 2014, pp. 750-769.
Tam, B. et al., "Indentification of an Outer Segment Targeting Signal in the COOH Terminus of Rhodopsin Using Transgenic *Xenopus laevis* ". The Journal of Cell Biology, 2000. vol. 151, No. 7. pp. 1369-1380.
Takahashi, et al. "Diversion of the Sign of Photoaxis in a *Chlamydomonas reinhardtu* Mutant Incorpoarted with Retinal and Its Analongs," FEBS Letters, 1992, vol. 314, No. 3, pp. 275-279.
Takahashi, et al., "Induction of Pluripotent Stem Cells from Mouse Embroyonic and Adult Fibroblast Cultures by Defined Factors", 2006, Cell, Vol. 126, pp. 663-676.
Tatarkiewwicz, et al. "Reversal of Hyperglycemia in Mice After Subcutaneoud Transplantation in Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human Ca,2.1 Current Density in Neurons", PNAS USA, 2002, vol. 99, No. 20: pp. 13284-13289.
Tsau et al. "Districuted Aspects of the Response to Siphon Touch in *Aplysia*: Spread of Stimulus Information and Cross-Correlation Analysis," The Journal of Neuroscience, 1994, vol. 14, No. 7. 4167-4184.
Tsai, et al., "Phasic Firing in Dopaminergic Neurons in Sufficient for Behavioral Conditioning", Science. 2009, vol. 324. pp. 1080-1084.
[No Authors Listed] "Two bright new faces in gene therapy," Nature Biotechnology, 1996, vol. 14, p. 556.
Tye et. al., "Amygdala circuitry mediating reversible and biodirectional control of anxiety", Nature, 2011, Vol. 471(7338): pp. 358-362.
Tye, et al. "Optogenetic investigation of neural circuits underlyding brain disease in animal models," Nture Reviews Neuroscience (Mar. 2012), 13(4):251-266.
Tye et. al., Supplementary Materials: "An optically-resolved microcircuit for bidirectional anxiety control", Nature. 2011. vol. 471(7338): pp. 358-362.
"Subname: Full=Channelrhodopsin-1", retrieved from EBI accession No. UNIPROT: B4Y103, Database accession No. B4Y103, Sep. 23, 2008.
Ulmanen, et al. "Transcription and translation of foreign genes in *Bacillus subtillis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-38.
Vanin, et al. "Development of high-titer retroviral producer cell lines by using Cre-mediated recombination," Journal of Virology, 1997, vol. 71. No. 10: pp. 7820-7826.
Vetter, et al. "Developlment of Microscale Implantable Neural Interface (MINI) Probe System." Proceedings of the 2005 IEEE. Engineering in Medicine and Biology 27th Annual Conference, Shanghai, China, Sep. 1-4, 2005.
Wagner, "Noninvasive Human Brain Stimulation", Annual Rev. Biomed. Eng. 2007, 9:19:1-19.39.
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.

Watson, et al. "Targeting transduction patterns in the mouse brain by lentivirus vectors pseudotyped with VSV, Ebola, Mokola, LCMV, or MuLV envelope proteins," Molecular Therapy. 2002, vol. 5, No. 5, pp. 528-537.
Wang et al, "Direct-current Nanogenerator Driven By Ultrasonic Waves," Science, 2007. vol. 316, pp. 102-105.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Wang et. al., "High-speed mapping of synaptic connectivity using photostimulation in Channelrhodopsin-2 transgenic mice", PNAS, 2007. vol. 104, No. 19, pp. 8143-8148.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23. No. 8. pp. 3446-3456.
Wells et al. "Application of Infrared light for *in vivo* neural stimulation,"Journal of Biomedical Optics. 2005, vol. 10(6), pp. 064003-1-064003-12.
Witten et. al., Supporting Online Material for: "Cholinergic Interneurons Control Local Circuit Activity and Cocaine Conditioning", Science. 2010. vol. 330: 17 pages.
Witten et. al., "Cholinergic Interneurons Control Local Circuit Activity and Concaine Conditioning", Science. 2010, vol. 330, No. 6011: pp. 1677-1681.
Xiong et al., "Interregional connectivity to primary motor cortex revealed using MRI resting state images", Hum Brain Mapp. 1999. 8(2-3):151-156.
Yamazoe, et al, "Efficient generation of dopaminergie neurons from mouse embryonic stem calls enclosed in hollow fibers", Biomaterials, 2006, vol. 27. pp. 4871-4880.
Yan et al., "Cloning and Characterization of Human $\beta,\beta$-Carotene-15, 15'-Dioxygenase that is Hight Expressed in Retinal Pigment Epithelium", Genomics. 2001, vol. 72: pp. 193-202.
Yizhar et. al., "Neocortical excitation/inhibition balance in information procession and social dysfunction", Nature. 2011. vol. 477, pp. 171-178; and Supplemental Materials; 41 pages.
Yoon, et al., "A micromachined silicon depth probe for multichannel neural recording," IEEE Transactions Biomedical Engineering, 200. vol. 47, No. 8. pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals,"Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al, "Photochemical gating of heterologous ion channels: Remote control over genetically designated populations of neurons", PNAS. 2003. vol. 100, No. 3: pp. 1352-1357.
Zhang, et al. "Channelrhodopsin-2 and optical control of excitable cells."Nature Methods,2006, vol. 3, No. 10. pp. 785-792.
Zhang, et al. "Red-Shifted Optogenetic Excitation: a Tool for Fast Neural Control Derived from *Volvox carteri*", Nature Neurosciences, 2008. vol. 11. No. 6. pp. 631-633.
Zhang "Multimodal fast optical interrogation of neural circuitry." Nature. 2007. vol. 446, pp. 633-641.
Zhang, et al., "The Microbial Opsin Family of Optogenetic Tools". Cell, 2001, vol. 147, No. 7, pp. 1146-1457.
Zhao, et al., "Improved Expression of Halorhodopsin for Light-Induced Silencing of Neuronal Activity". Brain Cell Biology, 2008, vol. 36 (1-4), pp. 141-154.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology. 1998. vol. 72. No. 12. pp. 9873-9880.
Tamai, "Progress in Pathogenesis and Therpeutic Research in Retinitis Pigmentosa and Age Related Macular Degeneration", NIPPON GANKA GAKKAI ZASSHI, Dec. 2004, 108(12):750-769.

(56) References Cited

OTHER PUBLICATIONS

Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.
Fiala et al., "Optogenetic approaches in neuroscience", Current Biology, Oct. 2010. 20(20):R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amugdala", Neurobiol Learning Mem, 87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *Drosophila* larvae", Current Biology, Sep. 2006, 16(17):1741-4747.
Brewin; "The Nature and Significant of Memory Disturbance in Posttraumatic Stress Disorder"; Ann. Rev. Clin. Psychol.; vol. 7, pp. 203-227 (2011).
Raper, et al.; "Fatal systemic inflammatory response syndrome in a ornithine transcarbamylase deficient patient following adenviral gene transfer." Mol. Genet. Metab.; Vol. 80, No. 1-2, pp. 148-158 (Sep.-Oct. 2003).
Samuelson; "Post-traumatic stress disorder and declarative memory functioning: a review"; Dialogues in Clinical Neuroscience; vol. 13, No. 3, pp. 346-351 (2011).
U.S. Appl. No. 13/882,703, filed Nov. 4, 2011, Deisseroth, et al.
U.S. Appl. No. 13/855,413, filed Apr. 2, 2013, Deisseroth, et al.
U.S. Appl. No. 14/219,547, filed Mar. 19, 2014, Deisseroth, et al.
Berndt et al., "Structure-Guided Transformation of Channelrhodopsin into a Light-Activated Chloride Channel", Science (Apr. 2014), 344(6182):420-424.
Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt9):2585-2612.
Garrido et al., "A Targetng motif involved in sodium channel clustering at the axonal initial segment", Science (Jun. 2003), 300(5628):2091-4.
Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al., "Virally mediated optogenetic excitation and inhibition of pain in freely moving nontransgenic mice", Nat Biotechnol , (Mar. 2014), 32(3):274-8.
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496 (7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety" Nature (Apr. 2013), 496(7444):219-23.
Kokel et al., "Photochemical activation of TRPA1 channels in neurons and animals", Nat Chem Biol (Apr. 2013), 9(4):257-63.
Lammel et al., "Input-specific control of reward and aversion in the ventral tegmental area", Nature (Nov. 2012), 491(7423):212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16(10)1161-5.
Mattis et al., "Principles for applying optogenetic tools derived from direct comparative analysis of microbial opsins", Nat Methods (Dec. 2011), 9(2)159-72.
Mourot et al., "Rapid Optical Control of Nociception with an Ion Channel Photoswitch", Nat Methods (Feb. 2012), 9(4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.
Towne et al., "Efficient transduction of non-human primate motor neurons after intramuscular delivery of recombinant AAV serotype 6", Gene Ther. (Jan. 2010), 17(1):141-6.
Towne et al., "Optogenetic control of targeted peripheral axons in freely moving animals", PLoS One (Aug. 2013), 8(8)e72691.
Towne et al., "Recombinant adeno-associated virus serotype 6 (rAAV2/6)-mediated gene transfer to nociceptive neurons through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5(177):177ps6.
Li et al., "Surface Expression of Kv1 Channels is Governed by a C-Terminal Motif", J. Biol. Chem. (2000), 275(16):11597-11602.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Varo et al., "Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Deisseroth, et al., "Controlling the Brain with Light", Scientific American, 2010, vol. 303, pp. 48-55.
Douglass, et al., "Escape Behavior Elicited by Single, Channelrhodopsin-2-evoked Spikes in Zebrafish Somatosensory Neurons", Curr Biol., 2008, vol 18, No. 15, pp. 1133-7.
Sineshchekov, et al., "Two Rhodopsins Mediate Photoaxis to Low and High Intensity Light in Chlamydomas Reinhardtil", PNAS, 2002, 2002, vol. 99, No. 13, pp. 8689-94.
Tønnese, et al., "Optogenetic Control of Epileptiform Activity", PNAS, 2009. vol. 106, No. 29, pp. 12162-7.
Berlanga, et a.; "Cholinergic Interneurons of the Nucleus Accumbens and Dorsal Striatum are Activated by the Self-Administration of Cocaine"; Neuroscience; vol. 120, pp. 1149-1156.
Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).
Packer, et al.; "Targeting Neurons and Photons of Optogenetics"; Nature Neuroscience; vol. 16, No. 7, pp. 805-815 (Jul. 2013).
Barchet, et al.; "Challenges and opportunities in CNS delivery of therapeutics for neurodegenerative diseases"; Expert Opinion on Drug Delivery; vol. 6, No. 3. pp. 211-225 (Mar. 16, 2009).
Bowers, et al.; "Genetic therpy for the nervous system"; Human Molecular Genetics; vol. 20, No. 1, pp. R28-R41 (2011).
Castagne, et al.; "Rodent Models of Depression: Forced Swim and Tail Suspension Behavioral Despair Test in Rats and Mice"; Current Protocols in Pharmacology; Supp. 49, Unit 5.8.1-5.8.14 (Jun. 2010).
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Haim, et al.; "Gene Therapy to the Nervous System"; Stem Cell and Gene-Based Therapy; Section 2, pp. 133-154 (2006).
Pandya, et al.; "Where in the Brain Is Depression?"; Curr. Psychiatry Rep.; vol. 14, pp. 634-642 (2012).
Stonehouse, et al.; "Caffeine Regulates Neuronal Expression of the Dopamine 2 Receptor Gene"; Molecular Pharmacology; vol. 63, No. 6, pp. 1463-1473 (2003).

(56) References Cited

OTHER PUBLICATIONS

Clark, et al.; "A future for transgenic livestock"; Nature Reviews Genetics; vol. 4, No. 10, pp. 825-833 (Oct. 2003).
Do Carmo, et al.; "Modeling Alzheimer's disease in transgenic rats"; Molecular Neurodegeneration; vol. 8, No. 37. 11 pages (2013).
Heymann, et al.; "Expression of Bacteriorhodopsin in Sf9 and COS-1 Cells"; Journal of Bioenergetics and Biomembranes; vol. 29, No. 1. pp. 55-59 (1997).
Ramalho, et al.; "Mouse genetic corneal disease resulting from transgenic insertional mutagenesis"; Br. J. Ophthalmol.; vol. 88, No. 3, pp. 428-432 (Mar. 2004).
Ristevski; "Making Better Transgenic Models: Conditional, Temporal, and Spatial Approaches"; Molecular Biotechnology; vol. 29, No. 2, pp. 153-163 (Feb. 2005).
Sigmund; "Viewpoint: Are Studies in Genetically Altered Mice Out of Control?"; Arterioscler Thromb Vasc. Biol.; vol. 20. No. 6, pp. 1425-1429 (Jun. 2000).
Sineshchekov et al.; "Intramolecular Proton Transfer in Channelrhodopsins"; Biophysical Journal; vol. 104, No. 4, pp. 807-807 (Feb. 2013).
Han, et al.; "Millisecond-Timescale Optical Control of Neural Dynamics in the Nonhuman Primate Brain"; Neuron; vol. 62. pp. 191-198 (Apr. 30, 2009).
Han, et a.; "Virogenetic and optogenetic machanisms to define potential therapeutic targets in psychiatric disorders"; Neuropharamcology; vol. 62. pp. 89-100 (2012).
Zhang, et al.; "Optogenetic interrogation of neural circuits: Technology for probing mammalian brain structures"; Nature Protocols: vol. 5, No. 3, pp. 439-456 (Mar. 1, 2010).
Ali; "Gene and stem cell therapy for retinal disorders"; vision-research.en—The Gateway to European Vision Researcg; accessed from http://www.vision-research.eu/index.php?id=696, 10 pages (accessed Jul. 24, 2015).
Asano, et al.; "Optically Controlled Contraction of Photosensitive Skeletal Muscle Cells"; Biotechnology & Bioengineering: vol. 109, No. 1, pp. 199-204 (January 2012).
Bruegmann, et al.; "Optogenetic control of heart muscle in vitro and in vivo"; Nature Methods; vol. 7. No. 11, pp. 897-900(Nov. 2010).
Bruegmann, et al.; "Optogenetics in cardiovascular research: a new tool for light-induced depolarization of cardiomyocytes and vascular smooth musle cells in vitro and in vivo"; European Heart Journal; vol. 32, No. Suppl . 1.p. 997 (Aug. 2011).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Mueller, et al.; "Clinical Gene Therapy Using Recominant Adeno-Assiciate Virus Vectors"; Gene Therapy; vol. 15, pp. 858-863 (2008).
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Ibbini, et al.; "A Field Conjugation Method for Direct Synthesis of Hyperthermia Phased-Array Heating Patterns"; IEEE Transactions on Ultrasonics, Ferroelectrics, and Frequency Control: vol. 36, No. 1. pp. 3-9 (Jan. 1989).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Wang, et al.; "Simultaneous phase and size control of upconversion nanocrystals throught lanthanide doping"; Nature; vol. 463, No. 7284. pp. 1061-1065 (Feb. 25, 2010).
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents: vol. 8. No. 1, pp. 53-69 (1998).
Edelstrin, et al.; "Gene therapy clincal trials worldwide 1989-2004—an overview"; The Journal of Gene Medicine: vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2011).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharamceutical Design; vol. 10, pp. 785-796 (2004).
Verma, et al.; "Gene therapy—promise, problems and prospects"; Nature; vol. 389, pp. 239-242 (Sep. 1997).
Jones, et al.; "Animal Models of Schizophrenia"; British Journal of Pharmacology; vol. 164, pp. 1162-1194 (2011).

\* cited by examiner wt ChR2  C128T  C128A  C128S

SEQUENCE LISTING

```
<160> NUMBER OF SEQ ID NOS: 16

<210> SEQ ID NO 1
<211> LENGTH: 354
<212> TYPE: PRT
<213> ORGANISM: Artificial Sequence
<220> FEATURE:
<223> OTHER INFORMATION: ChR2

<400> SEQUENCE: 1

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
```

```
                 50                  55                  60
Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                     85                  90                  95

Glu Phe Phe Phe Glu Phe Lys Asn Pro Ser Met Leu Tyr Leu Ala Thr
                    100                 105                 110

Gly His Arg Val Gln Trp Leu Arg Tyr Ala Glu Trp Leu Leu Thr Cys
                115                 120                 125

Pro Val Ile Leu Ile His Leu Ser Asn Leu Thr Gly Leu Ser Asn Asp
            130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Pro Met Met Gly His Phe Leu Arg Val Lys Ile
305                 310                 315                 320

His Glu His Ile Leu Leu Tyr Gly Asp Ile Arg Lys Lys Gln Lys Val
                325                 330                 335

Asn Val Ala Gly Gln Glu Met Glu Val Glu Thr Met Val His Glu Glu
                340                 345                 350

Asp Asp

<210> SEQ ID NO 2
<211> LENGTH: 300
<212> TYPE: PRT
<213> ORGANISM: artificial
<220> FEATURE:
<223> OTHER INFORMATION: VChR1 Protein

<400> SEQUENCE: 2

Met Asp Tyr Pro Val Ala Arg Ser Leu Ile Val Arg Tyr Pro Thr Asp
  1               5                  10                  15

Leu Gly Asn Gly Thr Val Cys Met Pro Arg Gly Gln Cys Tyr Cys Glu
                 20                  25                  30

Gly Trp Leu Arg Ser Arg Gly Thr Ser Ile Glu Lys Thr Ile Ala Ile
             35                  40                  45

Thr Leu Gln Trp Val Val Phe Ala Leu Ser Val Ala Cys Leu Gly Trp
 50                  55                  60
```

```
Tyr Ala Tyr Gln Ala Trp Arg Ala Thr Cys Gly Trp Glu Glu Val Tyr
 65                  70                  75                  80

Val Ala Leu Ile Glu Met Met Lys Ser Ile Ile Glu Ala Phe His Glu
                 85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 3
<211> LENGTH: 291
<212> TYPE: PRT
<213> ORGANISM: Artificial
<220> FEATURE:
<223> OTHER INFORMATION: Synthetic Construct Derived from Natronomonas
      pharaonis

<400> SEQUENCE: 3

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
```

```
                 115                 120                 125
Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp
    290

<210> SEQ ID NO 4
<211> LENGTH: 1599
<212> TYPE: DNA
<213> ORGANISM: Artificial Sequence
<220> FEATURE:
<223> OTHER INFORMATION: Humanized NpHR: the first 873bp; EYFP: the last
      717bp

<400> SEQUENCE: 4
atgacagaga ccctgcctcc cgtgaccgag agtgccgtgg cccttcaagc cgaggttacc          60
caaagggagt tgttcgagtt cgtgctgaac gaccctttgc ttgcaagcag tctctatatc        120
aacatcgcac ttgcaggact gagtatactg ctgttcgttt ttatgacccg aggactcgat        180
gatccacggg caaaacttat tgctgtgtca accatccttg tgcctgtcgt cagcattgcc        240
tcctacactg gattggcgag cggcctgaca atttccgttc ttgaaatgcc agcgggccat        300
tttgcagaag cagctcagt gatgctggga ggagaagagg tagatggtgt agtcaccatg        360
tggggacggt atctcacctg gcacttttcc acgcccatga ttctcctcgc tctgggtctc        420
ctggccggaa gcaatgctac aaagctcttc acagctatca ctttcgatat cgctatgtgc        480
gtgactggcc ttgccgcggc cctgactacc tcctcccacc tcatgagatg gttctggtac        540
gctatcagtt gtgcatgctt tctggtggtc ttgtatatcc tgctggtgga gtgggcacag        600
gacgccaaag ccgcgggaac cgctgacatg ttcaatacccc tgaagctgtt gacagtagtg        660
atgtggctgg ggtatccaat tgtgtgggct cttggagtcg agggtatcgc ggtgttgccc        720
gttggggtga cgagctgggg atattctttc ctggatatcg tggcaaagta cattttcgca        780
ttcttgctcc tgaactatct gacgtcaaac gaatctgtcg tgtccggcag catttttggat        840 gttccatctg cttctgggac cccggctgat gatgcggccg ccgtgagcaa gggcgaggag        900
ctgttcaccg gggtggtgcc catcctggtc gagctggacg gcgacgtaaa cggccacaag        960
ttcagcgtgt ccggcgaggg cgagggcgat gccacctacg gcaagctgac cctgaagttc       1020
```

```
atctgcacca ccggcaagct gcccgtgccc tggcccaccc tcgtgaccac cttcggctac    1080
ggcctgcagt gcttcgcccg ctaccccgac cacatgaagc agcacgactt cttcaagtcc    1140
gccatgcccg aaggctacgt ccaggagcgc accatcttct tcaaggacga cggcaactac    1200
aagacccgcg ccgaggtgaa gttcgagggc gacaccctgg tgaaccgcat cgagctgaag    1260
ggcatcgact tcaaggagga cggcaacatc ctggggcaca agctggagta caactacaac    1320
agccacaacg tctatatcat ggccgacaag cagaagaacg gcatcaaggt gaacttcaag    1380
atccgccaca acatcgagga cggcagcgtg cagctcgccg accactacca gcagaacacc    1440
cccatcggcg acggccccgt gctgctgccc gacaaccact acctgagcta ccagtccgcc    1500
ctgagcaaag accccaacga gaagcgcgat cacatggtcc tgctggagtt cgtgaccgcc    1560
gccgggatca ctctcggcat ggacgagctg tacaagtaa                          1599
```

<210> SEQ ID NO 5
<211> LENGTH: 1599
<212> TYPE: DNA
<213> ORGANISM: Artificial Sequence
<220> FEATURE:
<223> OTHER INFORMATION: Non-Humanized nhNpHR - EYFP

<400> SEQUENCE: 5

```
atgactgaga cattgccacc ggtaacggaa tcggctgttg cgctacaggc ggaggtgacc      60
cagagggagc tgttcgagtt cgttctcaac gaccccctcc tcgccagttc gctgtatatt     120
aatatcgcac tggcagggct gtcgatactg cttttcgtgt tcatgacgcg cggactcgac     180
gacccacggg cgaaactcat cgccgtttcg acgattttgg tgccggtggt ctctatcgcg     240
agctacaccg gccttgcatc ggggctcacc atcagcgtcc tcgagatgcc agccggccac     300
ttcgccgagg ggtcctcggt gatgctcggc ggcgaagagg tagacggcgt cgtgacgatg     360
tggggccgct atctgacgtg ggcccttttcg acaccgatga tactgctggc gcttgggctg     420
cttgctggct ctaacgccac gaagctcttt accgccatca ccttcgacat cgcgatgtgt     480
gtcaccggcc tcgcagccgc gctgacgacc tcttcgcacc tgatgcggtg gttctggtac     540
gccatcagtt gtgcgtgttt cctcgtcgtc ctctacatcc tgctcgtcga gtgggcacag     600
gacgccaagg ctgccggtac tgcggatatg ttcaatacgc tgaagctgct gaccgttgtc     660
atgtggctcg gctaccccat cgtgtgggca ctcggcgttg agggcatcgc cgttcttccg     720
gtcggagtca cgtcgtgggg atacagcttc ctcgacatcg tcgcgaagta catcttcgcg     780
ttcctgctgc tcaactacct cacgtcgaac gagagcgtca tctccggctc gatactcgac     840
gtgccgtccg cgtcgggcac tcccgctgac gacgcggccg ccgtgagcaa gggcgaggag     900
ctgttcaccg gggtggtgcc catcctggtc gagctggacg gcgacgtaaa cggccacaag     960
ttcagcgtgt ccggcgaggg cgagggcgat gccacctacg gcaagctgac cctgaagttc    1020
atctgcacca ccggcaagct gcccgtgccc tggcccaccc tcgtgaccac cttcggctac    1080
ggcctgcagt gcttcgcccg ctaccccgac cacatgaagc agcacgactt cttcaagtcc    1140
gccatgcccg aaggctacgt ccaggagcgc accatcttct tcaaggacga cggcaactac    1200
aagacccgcg ccgaggtgaa gttcgagggc gacaccctgg tgaaccgcat cgagctgaag    1260
ggcatcgact tcaaggagga cggcaacatc ctggggcaca agctggagta caactacaac    1320
agccacaacg tctatatcat ggccgacaag cagaagaacg gcatcaaggt gaacttcaag    1380
atccgccaca acatcgagga cggcagcgtg cagctcgccg accactacca gcagaacacc    1440
```

```
cccatcggcg acggccccgt gctgctgccc gacaaccact acctgagcta ccagtccgcc    1500
ctgagcaaag accccaacga gaagcgcgat cacatggtcc tgctggagtt cgtgaccgcc    1560
gccgggatca ctctcggcat ggacgagctg tacaagtaa                           1599
```

<210> SEQ ID NO 6
<211> LENGTH: 1641
<212> TYPE: DNA
<213> ORGANISM: Artificial Sequence
<220> FEATURE:
<223> OTHER INFORMATION: SP(nAChR-S) - hNpHR - EYFP

<400> SEQUENCE: 6

```
atgaggggta cgcccctgct cctcgtcgtc tctctgttct ctctgcttca ggacacagag     60
accctgcctc ccgtgaccga gagtgccgtg gcccttcaag ccgaggttac ccaaagggag    120
ttgttcgagt tcgtgctgaa cgacccttgg cttgcaagca gtctctatat caacatcgca    180
cttgcaggac tgagtatact gctgttcgtt tttatgaccc gaggactcga tgatccacgg    240
gcaaaactta ttgctgtgtc aaccatcctt gtgcctgtcg tcagcattgc ctcctacact    300
ggattggcga gcggcctgac aatttccgtt cttgaaatgc agcggggcca ttttgcagaa    360
ggcagctcag tgatgctggg aggagaagag gtagatggtg tagtcaccat gtggggacgg    420
tatctcacct gggcactttc cacgcccatg attctcctcg ctctgggtct cctggccgga    480
agcaatgcta caaagctctt cacagctatc actttcgata tcgctatgtg cgtgactggc    540
cttgccgcgg ccctgactac ctcctcccac ctcatgagat ggttctggta cgctatcagt    600
tgtgcatgct ttctggtggt cttgtatatc ctgctggtgg agtgggcaca ggacgccaaa    660
gccgcgggaa ccgctgacat gttcaatacc ctgaagctgt tgacagtagt gatgtggctg    720
gggtatccaa ttgtgtgggc tcttggagtc gagggtatcg cggtgttgcc cgttgggtg     780 acgagctggg gatattcttt cctggatatc gtggcaaagt acattttcgc attcttgctc    840
ctgaactatc tgacgtcaaa cgaatctgtc gtgtccggca gcattttgga tgttccatct    900
gcttctggga ccccggctga tgatgtgagc aagggcgagg agctgttcac cggggtggtg    960
cccatcctgg tcgagctgga cggcgacgta aacggccaca agttcagcgt gtccggcgag   1020
ggcgagggcg atgccaccta cggcaagctg accctgaagt tcatctgcac caccggcaag   1080
ctgcccgtgc cctggcccac cctcgtgacc accttcggct acggcctgca gtgcttcgcc   1140
cgctacccgg accacatgaa gcagcacgac ttcttcaagt ccgccatgcc cgaaggctac   1200
gtccaggagc gcaccatctt cttcaaggac gacggcaact acaagacccg cgccgaggtg   1260
aagttcgagg gcgacaccct ggtgaaccgc atcgagctga agggcatcga cttcaaggag   1320
gacggcaaca tcctggggca caagctggag tacaactaca acagccacaa cgtctatatc   1380
atggccgaca agcagaagaa cggcatcaag gtgaacttca agatccgcca caacatcgag   1440
gacggcagcg tgcagctcgc cgaccactac cagcagaaca cccccatcgg cgacggcccc   1500
gtgctgctgc ccgacaacca ctacctgagc taccagtccg ccctgagcaa agaccccaac   1560
gagaagcgcg atcacatggt cctgctggag ttcgtgaccg ccgccgggat cactctcggc   1620
atggacgagc tgtacaagta a                                             1641
```

<210> SEQ ID NO 7
<211> LENGTH: 1605
<212> TYPE: DNA
<213> ORGANISM: artificial
<220> FEATURE:
<223> OTHER INFORMATION: hNpHR - EYFP - ETQV

<400> SEQUENCE: 7

```
atgacagaga cccthcctcc cgtgaccgag agtgccgtgg cccttcaagc cgaggttacc        60
caaagggagt tgttcgagtt cgtgctgaac gacccttgc ttgcaagcag tctctatatc       120
aacatcgcac ttgcaggact gagtatactg ctgttcgttt tatgacccg aggactcgat       180
gatccacggg caaaacttat tgctgtgtca accatccttg tgcctgtcgt cagcattgcc       240
tcctacactg gattggcgag cggcctgaca atttccgttc ttgaaatgcc agcgggccat       300
tttgcagaag gcagctcagt gatgctggga ggagaagagg tagatggtgt agtcaccatg       360
tggggacggt atctcacctg gcactttcc acgcccatga ttctcctcgc tctgggtctc       420
ctggccggaa gcaatgctac aaagctcttc acagctatca ctttcgatat cgctatgtgc       480
gtgactggcc ttgccgcggc cctgactacc tcctcccacc tcatgagatg gttctggtac       540
gctatcagtt gtgcatgctt tctggtggtc ttgtatatcc tgctggtgga gtgggcacag       600
gacgccaaag ccgcgggaac cgctgacatg ttcaataccc tgaagctgtt gacagtagtg       660
atgtggctgg ggtatccaat tgtgtgggct cttggagtcg agggtatcgc ggtgttgccc       720
gttggggtga cgagctgggg atattctttc ctggatatcg tggcaaagta cattttcgca       780
ttcttgctcc tgaactatct gacgtcaaac gaatctgtcg tgtccggcag cattttggat       840
gttccatctg cttctgggac cccggctgat gatatggtga gcaagggcga ggagctgttc       900
accggggtgg tgcccatcct ggtcgagctg gacggcgacg taaacggcca agttcagc        960
gtgtccggcg agggcgaggg cgatgccacc tacggcaagc tgaccctgaa gttcatctgc      1020
accaccggca agctgcccgt gccctggccc accctcgtga ccaccttcgg ctacggcctg      1080
cagtgcttcg cccgctaccc cgaccacatg aagcagcacg acttcttcaa gtccgccatg      1140
cccgaaggct acgtccagga gcgcaccatc ttcttcaagg acgacggcaa ctacaagacc      1200
cgcgccgagg tgaagttcga gggcgacacc ctggtgaacc gcatcgagct gaagggcatc      1260
gacttcaagg aggacggcaa catcctgggg cacaagctgg agtacaacta caacagccac      1320
aacgtctata tcatggccga caagcagaag aacggcatca aggtgaactt caagatccgc      1380
cacaacatcg aggacggcag cgtgcagctc gccgaccact accagcagaa cacccccatc      1440
ggcgacggcc ccgtgctgct gcccgacaac cactacctga gctaccagtc cgccctgagc      1500
aaagacccca acgagaagcg cgatcacatg gtcctgctgg agttcgtgac cgccgccggg      1560
atcactctcg gcatggacga gctgtacaag gagacccagg tgtaa                      1605
```

<210> SEQ ID NO 8
<211> LENGTH: 1611
<212> TYPE: DNA
<213> ORGANISM: artificial
<220> FEATURE:
<223> OTHER INFORMATION: hNpHR - EYFP - actin

<400> SEQUENCE: 8

```
atgacagaga cccthcctcc cgtgaccgag agtgccgtgg cccttcaagc cgaggttacc        60
caaagggagt tgttcgagtt cgtgctgaac gacccttgc ttgcaagcag tctctatatc       120
aacatcgcac ttgcaggact gagtatactg ctgttcgttt tatgacccg aggactcgat       180
gatccacggg caaaacttat tgctgtgtca accatccttg tgcctgtcgt cagcattgcc       240
tcctacactg gattggcgag cggcctgaca atttccgttc ttgaaatgcc agcgggccat       300
tttgcagaag gcagctcagt gatgctggga ggagaagagg tagatggtgt agtcaccatg       360
```

```
tggggacggt atctcacctg gcactttcc acgcccatga ttctcctcgc tctgggtctc    420
ctggccggaa gcaatgctac aaagctcttc acagctatca ctttcgatat cgctatgtgc    480
gtgactggcc ttgccgcggc cctgactacc tcctcccacc tcatgagatg gttctggtac    540
gctatcagtt gtgcatgctt tctggtggtc ttgtatatcc tgctggtgga gtgggcacag    600
gacgccaaag ccgcgggaac cgctgacatg ttcaataccc tgaagctgtt gacagtagtg    660
atgtggctgg ggtatccaat tgtgtgggct cttggagtcg agggtatcgc ggtgttgccc    720
gttggggtga cgagctgggg atattctttc ctggatatcg tggcaaagta cattttcgca    780
ttcttgctcc tgaactatct gacgtcaaac gaatctgtcg tgtccggcag cattttggat    840
gttccatctg cttctgggac cccggctgat gatgcggccg ccgtgagcaa gggcgaggag    900
ctgttcaccg gggtggtgcc catcctggtc gagctggacg gcgacgtaaa cggccacaag    960
ttcagcgtgt ccggcgaggg cgagggcgat gccacctacg gcaagctgac cctgaagttc    1020
atctgcacca ccggcaagct gcccgtgccc tggcccaccc tcgtgaccac cttcggctac    1080
ggcctgcagt gcttcgcccg ctaccccgac cacatgaagc agcacgactt cttcaagtcc    1140
gccatgcccg aaggctacgt ccaggagcgc accatcttct tcaaggacga cggcaactac    1200
aagacccgcg ccgaggtgaa gttcgagggc gacaccctgg tgaaccgcat cgagctgaag    1260
ggcatcgact tcaaggagga cggcaacatc ctggggcaca gctggagta caactacaac    1320 agccacaacg tctatatcat ggccgacaag cagaagaacg gcatcaaggt gaacttcaag    1380
atccgccaca acatcgagga cggcagcgtg cagctcgccg accactacca gcagaacacc    1440
cccatcggcg acggccccgt gctgctgccc gacaaccact acctgagcta ccagtccgcc    1500
ctgagcaaag accccaacga gaagcgcgat cacatggtcc tgctggagtt cgtgaccgcc    1560
gccgggatca ctctcggcat ggacgagctg tacaagccga ccccgccgta a            1611
```

<210> SEQ ID NO 9
<211> LENGTH: 1605
<212> TYPE: DNA
<213> ORGANISM: artificial
<220> FEATURE:
<223> OTHER INFORMATION: hNpHR - EYFP - ERexport

<400> SEQUENCE: 9

```
atgacagaga ccctgcctcc cgtgaccgag agtgccgtgg cccttcaagc cgaggttacc     60
caaagggagt tgttcgagtt cgtgctgaac gaccctttgc ttgcaagcag tctctatatc    120
aacatcgcac ttgcaggact gagtatactg ctgttcgttt ttatgacccg aggactcgat    180
gatccacggg caaaacttat tgctgtgtca accatccttg tgcctgtcgt cagcattgcc    240
tcctacactg gattggcgag cggcctgaca atttccgttc ttgaaatgcc agcgggccat    300
tttgcagaag gcagctcagt gatgctggga ggagaagagg tagatggtgt agtcaccatg    360
tggggacggt atctcacctg gcactttcc acgcccatga ttctcctcgc tctgggtctc    420
ctggccggaa gcaatgctac aaagctcttc acagctatca ctttcgatat cgctatgtgc    480
gtgactggcc ttgccgcggc cctgactacc tcctcccacc tcatgagatg gttctggtac    540
gctatcagtt gtgcatgctt tctggtggtc ttgtatatcc tgctggtgga gtgggcacag    600
gacgccaaag ccgcgggaac cgctgacatg ttcaataccc tgaagctgtt gacagtagtg    660
atgtggctgg ggtatccaat tgtgtgggct cttggagtcg agggtatcgc ggtgttgccc    720
gttggggtga cgagctgggg atattctttc ctggatatcg tggcaaagta cattttcgca    780
ttcttgctcc tgaactatct gacgtcaaac gaatctgtcg tgtccggcag cattttggat    840
```

```
gttccatctg cttctgggac cccggctgat gatgtgagca agggcgagga gctgttcacc    900
ggggtggtgc ccatcctggt cgagctggac ggcgacgtaa acggccacaa gttcagcgtg    960
tccggcgagg gcgagggcga tgccacctac ggcaagctga ccctgaagtt catctgcacc   1020
accggcaagc tgcccgtgcc ctggcccacc ctcgtgacca ccttcggcta cggcctgcag   1080
tgcttcgccc gctaccccga ccacatgaag cagcacgact tcttcaagtc cgccatgccc   1140
gaaggctacg tccaggagcg caccatcttc ttcaaggacg acggcaacta caagacccgc   1200
gccgaggtga agttcgaggg cgacaccctg gtgaaccgca tcgagctgaa gggcatcgac   1260
ttcaaggagg acggcaacat cctggggcac aagctggagt acaactacaa cagccacaac   1320
gtctatatca tggccgacaa gcagaagaac ggcatcaagg tgaacttcaa gatccgccac   1380
aacatcgagg acggcagcgt gcagctcgcc gaccactacc agcagaacac ccccatcggc   1440
gacggccccg tgctgctgcc cgacaaccac tacctgagct accagtccgc cctgagcaaa   1500
gaccccaacg agaagcgcga tcacatggtc ctgctggagt tcgtgaccgc cgccgggatc   1560
actctcggca tggacgagct gtacaaggtg ctgggcagcc tgtaa                   1605

<210> SEQ ID NO 10
<211> LENGTH: 1644
<212> TYPE: DNA
<213> ORGANISM: artificial
<220> FEATURE:
<223> OTHER INFORMATION: SP(ChR2) - hNpHR - EYFP

<400> SEQUENCE: 10
atggattatg gaggcgccct gagtgccgtt gggcgcgagc tgctatttac agagaccctg     60
cctcccgtga ccgagagtgc cgtggcccct caagccgagg ttacccaaag ggagttgttc    120
gagttcgtgc tgaacgaccc tttgcttgca agcagtctct atatcaacat cgcacttgca    180
ggactgagta tactgctgtt cgtttttatg acccgaggac tcgatgatcc acgggcaaaa    240
cttattgctg tgtcaaccat ccttgtgcct gtcgtcagca ttgcctccta cactggattg    300
gcgagcggcc tgacaatttc cgttcttgaa atgccagcgg ccattttgc agaaggcagc    360
tcagtgatgc tgggaggaga agaggtagat ggtgtagtca ccatgtgggg acggtatctc    420
acctgggcac tttccacgcc catgattctc ctcgctctgg gtctcctggc cggaagcaat    480
gctacaaagc tcttcacagc tatcacttc gatatcgcta tgtgcgtgac tggccttgcc    540
gcggccctga ctacctcctc ccacctcatg atggttct ggtacgctat cagttgtgca    600
tgctttctgg tggtcttgta tatcctgctg gtggagtggg cacaggacgc caaagccgcg    660
ggaaccgctg acatgttcaa taccctgaag ctgttgacag tagtgatgtg gctggggtat    720
ccaattgtgt gggctcttgg agtcgagggt atcgcggtgt gcccgttgg ggtgacgagc    780
tggggatatt ctttcctgga tatcgtggca aagtacattt tcgcattctt gctcctgaac    840
tatctgacgt caaacgaatc tgtcgtgtcc ggcagcattt tggatgttcc atctgcttct    900
gggaccccgg ctgatgatgc ggccgccgtg agcaagggcg aggagctgtt caccggggtg    960
gtgcccatcc tggtcgagct ggacggcgac gtaaacggcc acaagttcag cgtgtccggc   1020
gagggcgagg gcgatgccac ctacggcaag ctgaccctga agttcatctg caccaccggc   1080
aagctgcccg tgccctggcc caccctcgtg accaccttcg gctacggcct gcagtgcttc   1140
gcccgctacc ccgaccacat gaagcagcac gacttcttca gtccgccat gcccgaaggc   1200
tacgtccagg agcgcaccat cttcttcaag gacgacggca actacaagac ccgcgccgag   1260
```

```
gtgaagttcg agggcgacac cctggtgaac cgcatcgagc tgaagggcat cgacttcaag      1320
gaggacggca acatcctggg gcacaagctg gagtacaact acaacagcca caacgtctat      1380
atcatggccg acaagcagaa gaacggcatc aaggtgaact tcaagatccg ccacaacatc      1440
gaggacggca gcgtgcagct cgccgaccac taccagcaga cacccccat cggcgacggc       1500 cccgtgctgc tgcccgacaa ccactacctg agctaccagt ccgccctgag caaagacccc      1560
aacgagaagc gcgatcacat ggtcctgctg gagttcgtga ccgccgccgg gatcactctc      1620
ggcatggacg agctgtacaa gtaa                                             1644

<210> SEQ ID NO 11
<211> LENGTH: 1665
<212> TYPE: DNA
<213> ORGANISM: artificial
<220> FEATURE:
<223> OTHER INFORMATION: SP(nAChR-L) - hNpHR - EYFP

<400> SEQUENCE: 11
atgggtcttc gtgctcttat gctttggctt cttgctgctg ctggtcttgt tcgtgaatct       60
cttcaaggta cagagaccct gcctcccgtg accgagagtg ccgtggccct tcaagccgag      120
gttacccaaa gggagttgtt cgagttcgtg ctgaacgacc ctttgcttgc aagcagtctc      180
tatatcaaca tcgcacttgc aggactgagt atactgctgt tcgtttttat gacccgagga      240
ctcgatgatc cacgggcaaa acttattgct gtgtcaacca tccttgtgcc tgtcgtcagc      300
attgcctcct acactggatt ggcgagcggc ctgacaattt ccgttcttga atgccagcg       360 ggccattttg cagaaggcag ctcagtgatg ctgggaggag aagaggtaga tggtgtagtc      420
accatgtggg gacggtatct cacctgggca cttttccacgc ccatgattct cctcgctctg      480
ggtctcctgg ccgaagcaa tgctacaaag ctcttcacag ctatcacttt cgatatcgct       540
atgtgcgtga ctggccttgc gcgggccctg actacctcct cccacctcat gagatggttc      600
tggtacgcta tcagttgtgc atgctttctg gtggtcttgt atatcctgct ggtggagtgg      660
gcacaggacg ccaaagccgc gggaaccgct gacatgttca ataccctgaa gctgttgaca      720
gtagtgatgt ggctggggta tccaattgtg tgggctcttg gagtcgaggg tatcgcggtg      780
ttgcccgttg gggtgacgag ctggggatat tctttcctgg atatcgtggc aaagtacatt      840
ttcgcattct tgctcctgaa ctatctgacg tcaaacgaat ctgtcgtgtc cggcagcatt      900
ttggatgttc catctgcttc tgggaccccg gctgatgatg cggccgccgt gagcaagggc      960
gaggagctgt tcaccggggt ggtgcccatc ctggtcgagc tggacggcga cgtaaacggc     1020
cacaagttca gcgtgtccgg cgagggcgag ggcgatgcca cctacggcaa gctgaccctg     1080
aagttcatct gcaccaccgg caagctgccc gtgccctggc ccaccctcgt gaccaccttc     1140
ggctacggcc tgcagtgctt cgcccgctac cccgaccaca tgaagcagca cgacttcttc     1200
aagtccgcca tgcccgaagg ctacgtccag gagcgcacca tcttcttcaa ggacgacggc     1260
aactacaaga cccgcgccga ggtgaagttc gagggcgaca ccctggtgaa ccgcatcgag     1320
ctgaagggca tcgacttcaa ggaggacggc aacatcctgg ggcacaagct ggagtacaac     1380
tacaacagcc acaacgtcta tatcatggcc gacaagcaga gaacggcat caaggtgaac      1440 ttcaagatcc gccacaacat cgaggacggc agcgtgcagc tcgccgacca ctaccagcag    1500 aacacccca tcggcgacgg ccccgtgctg ctgcccgaca accactacct gagctaccag      1560
tccgccctga gcaaagaccc caacgagaag cgcgatcaca tggtcctgct ggagttcgtg     1620
accgccgccg ggatcactct cggcatggac gagctgtaca agtaa                    1665
```

<210> SEQ ID NO 12
<211> LENGTH: 1605
<212> TYPE: DNA
<213> ORGANISM: artificial
<220> FEATURE:
<223> OTHER INFORMATION: hNpHR-EYFP-VSNL

<400> SEQUENCE: 12

| | |
|---|---|
| atgacagaga ccctgcctcc cgtgaccgag agtgccgtgg cccttcaagc cgaggttacc | 60 |
| caaagggagt tgttcgagtt cgtgctgaac gaccctttgc ttgcaagcag tctctatatc | 120 |
| aacatcgcac ttgcaggact gagtatactg ctgttcgttt ttatgacccg aggactcgat | 180 |
| gatccacggg caaaacttat tgctgtgtca accatccttg tgcctgtcgt cagcattgcc | 240 |
| tcctacactg gattggcgag cggcctgaca atttccgttc ttgaaatgcc agcgggccat | 300 |
| tttgcagaag gcagctcagt gatgctggga ggagaagagg tagatggtgt agtcaccatg | 360 |
| tggggacggt atctcacctg gcacttttcc acgcccatga ttctcctcgc tctgggtctc | 420 |
| ctggccggaa gcaatgctac aaagctcttc acagctatca ctttcgatat cgctatgtgc | 480 |
| gtgactggcc ttgccgcggc cctgactacc tcctcccacc tcatgagatg gttctggtac | 540 |
| gctatcagtt gtgcatgctt tctggtggtc ttgtatatcc tgctggtgga gtgggcacag | 600 |
| gacgccaaag ccgcgggaac cgctgacatg ttcaataccc tgaagctgtt gacagtagtg | 660 |
| atgtggctgg ggtatccaat tgtgtgggct cttggagtcg agggtatcgc ggtgttgccc | 720 |
| gttggggtga cgagctgggg atattctttc ctggatatcg tggcaaagta cattttcgca | 780 |
| ttcttgctcc tgaactatct gacgtcaaac gaatctgtcg tgtccggcag cattttggat | 840 |
| gttccatctg cttctgggac cccggctgat gatatggtga gcaagggcga ggagctgttc | 900 |
| accggggtgg tgcccatcct ggtcgagctg gacggcgacg taaacggcca agttcagc | 960 |
| gtgtccggcg agggcgaggg cgatgccacc tacggcaagc tgaccctgaa gttcatctgc | 1020 |
| accaccggca agctgcccgt gccctggccc accctcgtga ccaccttcgg ctacggcctg | 1080 |
| cagtgcttcg cccgctaccc cgaccacatg aagcagcacg acttcttcaa gtccgccatg | 1140 |
| cccgaaggct acgtccagga gcgcaccatc ttcttcaagg acgacggcaa ctacaagacc | 1200 |
| cgcgccgagg tgaagttcga gggcgacacc ctggtgaacc gcatcgagct gaagggcatc | 1260 |
| gacttcaagg aggacggcaa catcctgggg cacaagctgg agtacaacta caacagccac | 1320 |
| aacgtctata tcatggccga caagcagaag aacggcatca aggtgaactt caagatccgc | 1380 |
| cacaacatcg aggacggcag cgtgcagctc gccgaccact accagcagaa cacccccatc | 1440 |
| ggcgacggcc ccgtgctgct gcccgacaac cactacctga gctaccagtc cgccctgagc | 1500 |
| aaagacccca acgagaagcg cgatcacatg gtcctgctgg agttcgtgac cgccgccggg | 1560 |
| atcactctcg gcatggacga gctgtacaag gtgagcaacc tgtaa | 1605 |

<210> SEQ ID NO 13
<211> LENGTH: 1599
<212> TYPE: DNA
<213> ORGANISM: artificial
<220> FEATURE:
<223> OTHER INFORMATION: SP(nAChR-S) - hNpHR - EYFP - ERexport

<400> SEQUENCE: 13

| | |
|---|---|
| atgacagaga ccctgcctcc cgtgaccgag agtgccgtgg cccttcaagc cgaggttacc | 60 |
| caaagggagt tgttcgagtt cgtgctgaac gaccctttgc ttgcaagcag tctctatatc | 120 |

```
aacatcgcac ttgcaggact gagtatactg ctgttcgttt ttatgacccg aggactcgat    180
gatccacggg caaaacttat tgctgtgtca accatccttg tgcctgtcgt cagcattgcc    240
tcctacactg gattggcgag cggcctgaca atttccgttc ttgaaatgcc agcgggccat    300
tttgcagaag gcagctcagt gatgctggga ggagaagagg tagatggtgt agtcaccatg    360
tggggacggt atctcacctg gcactttcc acgcccatga ttctcctcgc tctgggtctc    420
ctggccggaa gcaatgctac aaagctcttc acagctatca ctttcgatat cgctatgtgc    480
gtgactggcc ttgccgcggc cctgactacc tcctcccacc tcatgagatg gttctggtac    540
gctatcagtt gtgcatgctt tctggtggtc ttgtatatcc tgctggtgga gtgggcacag    600
gacgccaaag ccgcgggaac cgctgacatg ttcaataccc tgaagctgtt gacagtagtg    660
atgtggctgg ggtatccaat tgtgtgggct cttggagtcg agggtatcgc ggtgttgccc    720
gttggggtga cgagctgggg atattctttc ctggatatcg tggcaaagta cattttcgca    780
ttcttgctcc tgaactatct gacgtcaaac gaatctgtcg tgtccggcag cattttggat    840
gttccatctg cttctgggac cccggctgat gatgcggccg ccgtgagcaa gggcgaggag    900
ctgttcaccg gggtggtgcc catcctggtc gagctggacg gcgacgtaaa cggccacaag    960
ttcagcgtgt ccggcgaggg cgagggcgat gccacctacg gcaagctgac cctgaagttc   1020
atctgcacca ccggcaagct gcccgtgccc tggcccaccc tcgtgaccac cttcggctac   1080
ggcctgcagt gcttcgcccg ctaccccgac cacatgaagc agcacgactt cttcaagtcc   1140
gccatgcccg aaggctacgt ccaggagcgc accatcttct tcaaggacga cggcaactac   1200
aagacccgcg ccgaggtgaa gttcgagggc gacacccctg gtgaaccgcat cgagctgaag   1260 ggcatcgact tcaaggagga cggcaacatc ctggggcaca gctggagta caactacaac   1320 agccacaacg tctatatcat ggccgacaag cagaagaacg gcatcaaggt gaacttcaag   1380
atccgccaca acatcgagga cggcagcgtg cagctcgccg accactacca gcagaacacc   1440
cccatcggcg acggccccgt gctgctgccc gacaaccact acctgagcta ccagtccgcc   1500
ctgagcaaag accccaacga aagcgcgat cacatggtcc tgctggagtt cgtgaccgcc   1560
gccgggatca ctctcggcat ggacgagctg tacaagtaa                          1599
```

```
<210> SEQ ID NO 14
<211> LENGTH: 23
<212> TYPE: PRT
<213> ORGANISM: Artificial Sequence
<220> FEATURE:
<223> OTHER INFORMATION: Synthetic amino acid sequence

<400> SEQUENCE: 14

Asn Lys Thr Val Trp Leu Arg Tyr Ala Glu Trp Leu Leu Thr Cys Pro
1               5                   10                  15

Val Ile Leu Ile His Leu Ser
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic amino acid sequence

<400> SEQUENCE: 15

His Arg Val Gln Trp Leu Arg Tyr Ala Glu Trp Leu Leu Thr Cys Pro
1               5                   10                  15
```

-continued

```
Val Ile Leu Ile His Leu Ser
            20

<210> SEQ ID NO 16
<211> LENGTH: 23
<212> TYPE: PRT
<213> ORGANISM: Artificial Sequence
<220> FEATURE:
<223> OTHER INFORMATION: Synthetic amino acid sequence

<400> SEQUENCE: 16

Asn Gly Val Val Trp Met Arg Tyr Gly Glu Trp Leu Leu Thr Cys Pro
1               5                   10                  15

Val Leu Leu Ile His Leu Ser
            20
```

OPTICALLY-BASED STIMULATION OF TARGET CELLS AND MODIFICATIONS THERETO

RELATED DOCUMENTS

This application is a divisional of U.S. patent application Ser. No. 13/128,979, filed Jul. 28, 2011, now U.S. Pat. No. 8,716,447, which is a national stage filing under 35 U.S.C. §371 of International Patent Application PCT/US2009/064355, filed Nov. 13, 2009, which claims benefit, under 35 U.S.C. §119(e), of U.S. Provisional Patent Application Ser. No. 61/114,781 filed on Nov. 14, 2008, and entitled "Systems, Methods and Compositions for Optical Stimulation of Target Cells and for Modifications Thereto". The contents of U.S. patent application Ser. No. 13/128,979, International Patent Application PCT/US2009/064355, and U.S. patent application Ser. No 61/114,781, including the Appendices filed therewith, are incorporated herein by reference in their entirety.

INCORPORATION-BY-REFERENCE OF MATERIAL SUBMITTED ELECTRONICALLY

Incorporated by reference in its entirety is a computer-readable nucleotide/amino acid sequence listing submitted concurrently herewith, and identified as follows: One 31,298 Byte ASCII (Text) file named "stfd225pct_ST25" created on Nov. 13, 2009.

FIELD OF THE INVENTION

The present invention relates generally to systems and approaches for stimulating target cells, and more particularly to using optics to stimulate the target cells.

BACKGROUND AND SUMMARY

The stimulation of various cells of the body has been used to produce a number of beneficial effects. One method of stimulation involves the use of electrodes to introduce an externally generated signal into cells. One problem faced by electrode-based brain stimulation techniques is the distributed nature of neurons responsible for a given mental process. Conversely, different types of neurons reside close to one another such that only certain cells in a given region of the brain are activated while performing a specific task. Alternatively stated, not only do heterogeneous nerve tracts move in parallel through tight spatial confines, but the cell bodies themselves may exist in mixed, sparsely embedded configurations. This distributed manner of processing seems to defy the best attempts to understand canonical order within the central nervous system (CNS), and makes neuromodulation a difficult therapeutic endeavor. This architecture of the brain poses a problem for electrode-based stimulation because electrodes are relatively indiscriminate with regards to the underlying physiology of the neurons that they stimulate. Instead, physical proximity of the electrode poles to the neuron is often the single largest determining factor as to which neurons will be stimulated. Accordingly, it is generally not feasible to absolutely restrict stimulation to a single class of neuron using electrodes.

Another issue with the use of electrodes for stimulation is that because electrode placement dictates which neurons will be stimulated, mechanical stability is frequently inadequate, and results in lead migration of the electrodes from the targeted area. Moreover, after a period of time within the body, electrode leads frequently become encapsulated with glial cells, raising the effective electrical resistance of the electrodes, and hence the electrical power delivery required to reach targeted cells. Compensatory increases in voltage, frequency or pulse width, however, may spread the electrical current and increase the unintended stimulation of additional cells.

Another method of stimulus uses photosensitive bio-molecular structures to stimulate target cells in response to light. For instance, light activated proteins can be used to control the flow of ions through cell membranes. By facilitating or inhibiting the flow of positive or negative ions through cell membranes, the cell can be briefly depolarized, depolarized and maintained in that state, or hyperpolarized. Neurons are an example of a type of cell that uses the electrical currents created by depolarization to generate communication signals (i.e., nerve impulses). Other electrically excitable cells include skeletal muscle, cardiac muscle, and endocrine cells. Neurons use rapid depolarization to transmit signals throughout the body and for various purposes, such as motor control (e.g., muscle contractions), sensory responses (e.g., touch, hearing, and other senses) and computational functions (e.g., brain functions). Thus, the control of the depolarization of cells can be beneficial for a number of different purposes, including (but not limited to) psychological therapy, muscle control and sensory functions.

Depending upon the application, particular characteristics of the responsiveness of the electrical stimulus and/or current flow can be important. Example characteristics include the duration the electrical current continues after light stimulus has been removed, delays between the light stimulus and the beginning of the flow of ions and the intensity or wavelength of the light necessary to cause (or inhibit) ion flow.

SUMMARY

Various aspects of the present invention are directed to devices, methods and systems related light-activated proteins in a manner that addresses challenges including those discussed above.

According to a first example embodiment, the present invention is directed to step-function opsins (SFOs) that provide relatively long on-times in response to light at a first wavelength. These SFOs can also respond to light of a second wavelength by turning-off, thereby functioning as a bi-stable switch.

Consistent with certain embodiments, one or more SFOs function as light-gated membrane channels when expressed in a neuronal cell. Activation of the SFOs moves the membrane voltage/resting potential of the neuronal cell towards the action potential threshold of the cell (e.g., depolarizes the cell), thereby facilitating action potentials therein.

According to a specific embodiment, aspects of the present invention are directed towards use of SFOs to characterize or treat diseases associated with neurology or the central nervous system (CNS). Particular aspects relate to use of SFOs to provide targeted excitation of neural populations for treatment or characterization of diseases. Other aspects relate to characterizations of neural circuitry and, in some cases, related behavioral responses.

Consistent with an embodiment, aspects of the present invention are directed toward mutations/substitutions of amino acids of opsins. This can include molecules coding for the mutant opsin and/or the mutant opsin itself. In a particular example, the embodiments include substitutions that affect the on-time and/or the on-current of the opsins. For instance, substitutions can be made to ChR2 or VChR1. In a particular implementation this can include, using ChR2 as example, substitutions at C128 and or D156. Homologous substitutions can be made to VChR1. These and other substitutions can be used alone or in combinations.

According to another embodiment, aspects of the present invention are directed toward a medicament for treatment of a neurological or CNS-based disease. The medicament is designed to introduce a mutant opsin to a patient. The introduced opsin can then be controlled through the application of light thereto as part of a treatment regimen.

Consistent with certain embodiments, aspects of the present invention are directed toward expression of multiple opsin-types within different neural populations and/or within the same cell. In one implementation, the opsins-types have respectively different responsiveness to light frequency/wavelengths, thereby allowing for individual control of each type through wavelength control of the stimulating light. In some implementations, the opsin-types have different temporal properties, different conductive properties and/or hyperpolarize or depolarize, respectively.

Another embodiment relates to aspects of the present invention that are directed to a method for treatment of a disorder. The method uses both SFOs and inhibitory molecules to selectively encourage or inhibit neurons. The method targets a group of neurons associated with the disorder; and in this group, the method includes engineering an inhibitory protein/molecule that uses an endogenous cofactor to respond to light by producing an inhibitory current to dissuade depolarization of the neurons. The method also includes engineering SFOs in neurons, of the same group and/or of a different group. The engineered neurons are then exposed to light, thereby dissuading and/or encouraging depolarization of the neurons.

The above summary is not intended to describe each embodiment or every implementation of the present disclosure. The figures and detailed description that follow more particularly exemplify various embodiments.

BRIEF DESCRIPTION OF THE DRAWINGS

The invention may be more completely understood in consideration of the detailed description of various embodiments of the invention that follows in connection with the accompanying drawings, in which:

FIG. 4b shows inactivation spectra for ChR2 (C128A/H134R) and VChR1 (C123S), and more particularly.

Figure 1A:
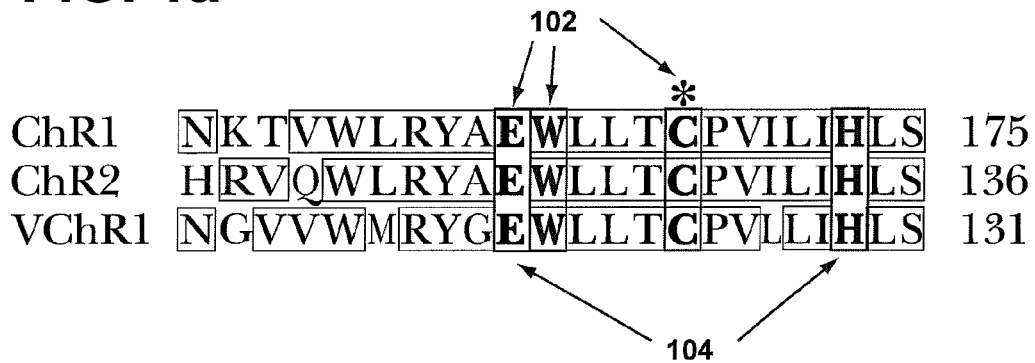
FIG. 1a shows the alignment of Helix 3 of several channelrhodopsins relative to bacteriorhodopsin (BR) from H. salinarum. Conserved residues are shown by a highlighted background, amino acids interacting with the chromophore are indicated by 102, and the ChR2 C128 is marked by an asterisk (*) Amino acids that serve as H+ donor or acceptor for RSB deprotonation and reprotonation are indicated by 104. ChR1 (SEQ ID NO:14); ChR2 (SEQ ID NO:15); VChR1 (SEQ ID NO:16).

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for facilitating practical application of a variety of photosensitive bio-molecular structures, and the invention has been found to be particularly suited for use in arrangements and methods dealing with cellular membrane voltage control and stimulation. While the present invention is not necessarily limited to such applications, various aspects of the invention may be appreciated through a discussion of various examples using this context.

Consistent with one example embodiment of the present invention, a light-responsive protein/molecule is engineered in a cell. The protein affects a flow of ions across the cell membrane in response to light. This change in ion flow creates a corresponding change in the electrical properties of the cells including, for example, the voltage and current flow across the cell membrane. In one instance, the protein functions in vivo using an endogenous cofactor to modify ion flow across the cell membrane. In another instance, the protein changes the voltage across the cell membrane so as to dissuade action potential firing in the cell. In yet another instance, the protein is capable of changing the electrical properties of the cell within several milliseconds of the light being introduced. Embodiments of the present invention relate to specific mutations of such light-activated proteins/molecules. These mutations include substitutions of one or more amino acids within the protein thereby producing surprising results as evidenced by the experimental data provided herein. These substitutions can be implemented by modifying a nucleotide sequence for coding a protein/molecule. Certain implementations relate to designing the nucleotide sequence for expression in a mammalian neuronal cell.

For details on delivery of such proteins, reference may be made to U.S. patent application Ser. No. 11/459,636 filed on Jul. 24, 2006 and entitled "Light-Activated Cation Channel and Uses Thereof", which is fully incorporated herein by reference.

Aspects of certain embodiments of the present invention are directed toward identification and modification of specific portions of light-gated channels. These modifications involve identifying key portions of the channels. The channels can be identified using high resolution imaging of the tertiary structure of the channel. Alternatively, knowledge of the structure of similar channels can be used. The following description provides details of a specific experimental implementation and methodology. The present invention is not limited to any one implementation and can be implemented for a number of different molecular modifications at various locations consistent with the teachings herein.

Specific aspects of the present invention relate to microbial opsin genes adapted for neuroscience, allowing transduction of light pulse trains into millisecond-timescale membrane potential changes in specific cell types within the intact mammalian brain (e.g., channelrhodopsin (ChR2), an example of which is provided as SEQ ID No. 1, Volvox channelrhodopsin (VChR1), an example of which is provided as SEQ ID No. 2, and halorhodopsin (NpHR), an example of which is provided as SEQ ID No. 3). ChR2 is a rhodopsin derived from the unicellular green alga *Chlamydomonas reinhardtii*. The term "rhodopsin" as used herein is a protein that comprises at least two building blocks, an opsin protein, and a covalently bound cofactor, usually retinal (retinaldehyde). The rhodopsin ChR2 is derived from the opsin Channelopsin-2 (Chop2), originally named Chlamyopsin-4 (Cop4) in the *Chlamydomonas* genome. The temporal properties of one depolarizing channelrhodopsin, ChR2, include fast kinetics of activation and deactivation, affording generation of precisely timed action potential trains. For applications seeking long timescale activation, it has been discovered that the normally fast off-kinetics of the channelrhodopsins can be slowed. For example, certain implementations of channelrhodopsins apply 1 mW/mm2 light for virtually the entire time in which depolarization is desired, which can be less than desirable.

Much of the discussion herein is directed to ChR2. Unless otherwise stated, the invention includes a number of similar variants. Examples include, but are not limited to, Chop2, ChR2-310, Chop2-310, and Volvox channelrhodopsin (VChR1), an example of which is provided as SEQ ID No. 2. For further details on VChR1 reference can be made to "Red-shifted optogenetic excitation: a tool for fast neural control derived from Volvox carteri," Nat Neurosci. June 2008, 11(6):631-3. Epub 2008 Apr. 23, which is fully incorporated herein by reference. In other implementations similar modifications can be made to other opsin molecules. For instance, modifications/mutations can be made to ChR2 or VChR1 variants. Moreover the modified variants can be used in combination with light-activated ion pumps including, but not limited to, molecules corresponding to sequences SEQ ID Nos. 3-13.

Embodiments of the present invention include relatively minor amino acid variants of the naturally occurring sequences. In one instance, the variants are greater than about 75% homologous to the protein sequence of the naturally occurring sequences. In other variants, the homology is greater than about 80%. Yet other variants have homology greater than about 85%, greater than 90%, or even as high as about 93% to about 95% or about 98%. Homology in this context means sequence similarity or identity, with identity being preferred. This homology can be determined using standard techniques known in the art. The compositions of embodiments of the present invention include the protein and nucleic acid sequences provided herein including variants which are more than about 50% homologous to the provided sequence, more than about 55% homologous to the provided sequence, more than about 60% homologous to the provided sequence, more than about 65% homologous to the provided sequence, more than about 70% homologous to the provided sequence, more than about 75% homologous to the provided sequence, more than about 80% homologous to the provided sequence, more than about 85% homologous to the provided sequence, more than about 90% homologous to the provided sequence, or more than about 95% homologous to the provided sequence.

As used herein, stimulation of a target cell is generally used to describe modification of properties of the cell. For instance, the stimulus of a target cell may result in a change in the properties of the cell membrane that can lead to the depolarization or polarization of the target cell. In a particular instance, the target cell is a neuron and the stimulus affects the transmission of impulses by facilitating or inhibiting the generation of impulses (action potentials) by the neuron.

A specific embodiment of the present invention relates to the generation of bi-stable (e.g., having extended conducting and non-conducting states in the absence of optical stimulus) channelrhodopsins that are gated into the active state with a single brief pulse of light while remaining active for a duration significantly longer than the light pulse. Such channelrhodopsins effectively process the delta function of light into a step function of membrane potential. These and other characteristics can be particularly useful for long-timescale, neuromodulatory, developmental, and preclinical/clinical applications including those where an exogenous chemical cofactor is not desirable (e.g., in vivo applications).

Aspects of certain embodiments of the present invention are directed toward controlled termination of the resulting stable depolarization at a specified time, particularly where the offset of termination of the depolarization is significantly delayed from the end of the triggering light pulse. For instance, the activation of opsins can temporarily shift the membrane resting potential of a neuron toward the action potential threshold voltage, thereby increasing action potentials therein. Deactivation of the same opsins restores the action potential to the "normal" resting potential. This deactivation can be implemented through optical stimulation of the appropriate frequency and intensity.

Figure 1B:
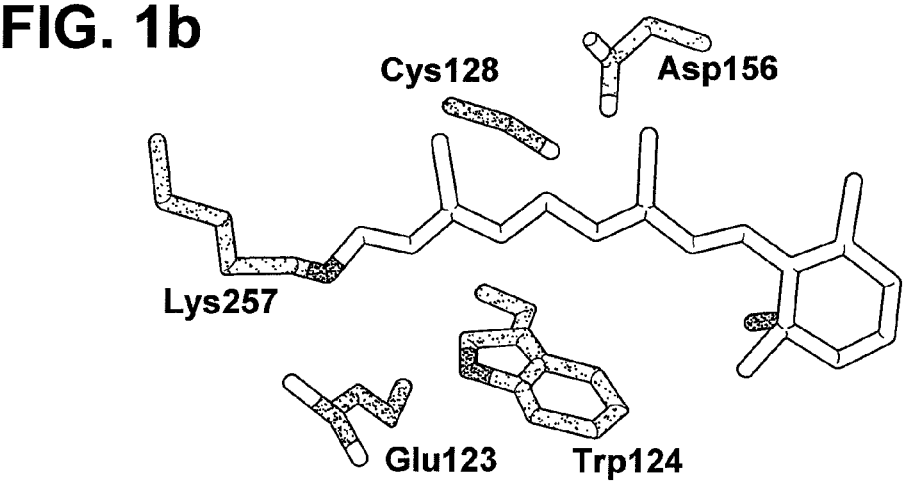
FIG. 1b shows a ChR2 chromophore model, based on the BR X-ray structure (1KGB13), with E123, C128, and D156 of ChR2 replacing D85, T90, and D118 of BR.

Embodiments of the present invention relate to one or more modifications of ChR2 to thereby affect the protein residues in manners that affect the channel kinetics. Embodiments of the present invention provide a mechanism for generating a host of modifications to light gated channels and pumps. Sequence comparisons to similar channels/pumps, such as the prokaryotic proton pump bacteriorhodopsin (BR), for which the tertiary structure is available at high resolution, are used to identify locations for modification. For example, structural inferences from BR, of the seven putative transmembrane helices in microbial rhodopsins, indicated that helix 3 is likely to contain the most amino acids likely to interact with the all-trans retinal Schiff base (RSB) chromophore and thus govern channel gating. Many of these amino acids are conserved in channelrhodopsins (FIG. 1a), suggesting that the RSB switch that governs interconversion of non-conducting and conducting states is also highly conserved. Mutations that interfere with the RSB therefore are potential candidates, not only for color tuning but also for altered kinetics and accumulation of the conducting state. Among the amino acids that interact with the RSB, the most notable sequence difference between BR and ChR2 is the Cys128 residue of ChR2, corresponding to Thr90 in BR. High resolution X-ray crystallography has shown that Thr90 in BR is located close to the C11/C12 carbons of the protonated RSB (FIG. 1b). Mutation of Thr90 to Ala or Val in BR results in a slowing of channel kinetics and accumulation of the M and O photocycle states. Thus, embodiments of the present invention relate to a modification of C128 to control channel kinetics.

Figure 1C:
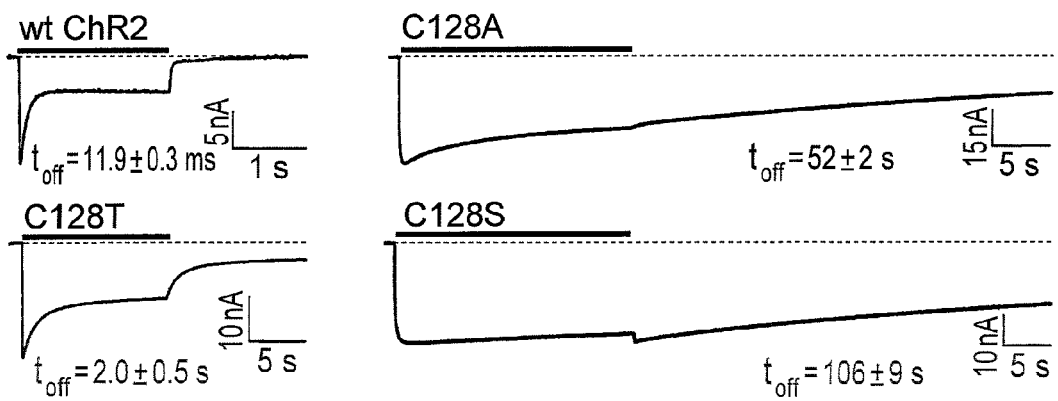
FIG. 1c shows photocurrents recorded from ChR2 wild type (wt), C128T, C128A and C128S expressed in *Xenopus* oocytes at 100 mM NaCl, pH 7.4 and −50 mV in response to 450 nm light pulses, 240 mW cm$^{-2}$. Time constants shown are for the decay of current after termination of blue light stimulation (mean±s.e.m.; n=3 cells for each trace).
Figure 1D:
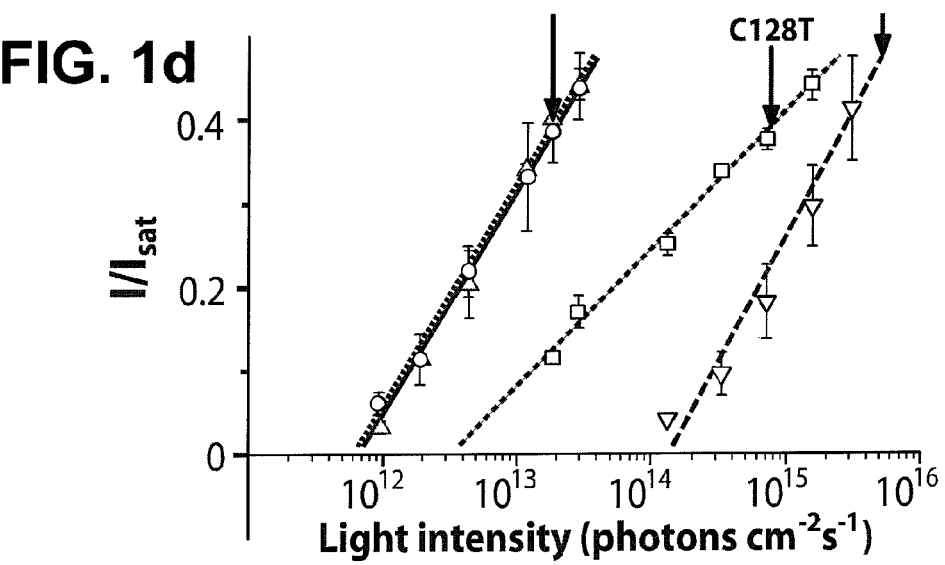
FIG. 1d shows the light dependence of the steady-state photocurrents recorded at low light intensities; cells expressing C128A and S are ~300-fold more sensitive than those that express wt ChR2. Amplitudes were normalized to the response at saturating light (I/ISat).
Figure 1E:
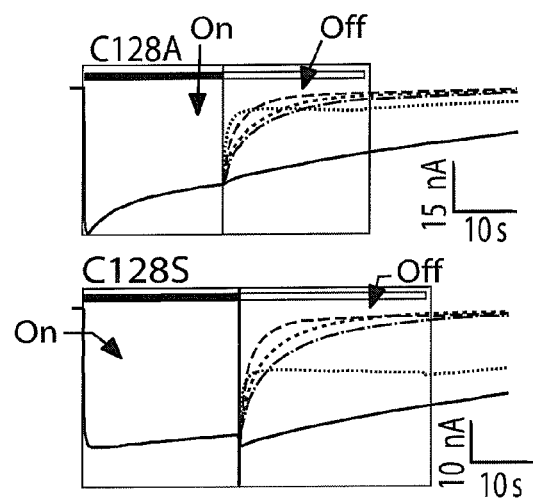
FIG. 1e shows photocurrents recorded from C128A and C128S mutants. Off kinetics were accelerated when a second (off) light pulse with longer wavelength followed the excitation (on) pulse (traces: 530 nm; 546 nm; 570 nm; 600 nm).
Figure 1F:
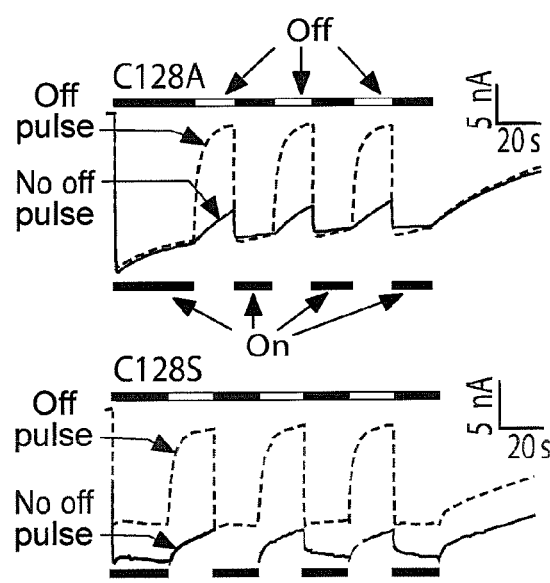
FIG. 1f shows responses to alternating 450 nm and 546 nm light pulses (Off pulse) or 450 nm light pulses only (No off pulse) in oocytes expressing C128A and C128S. Bars on top and bottom indicate light stimulation protocols for alternating blue/green (On/Off) and blue-only (On-only) traces respectively.

In an example implementation, channelrhodopsins was modified by replacing C128 by Thr, Ala, or Ser. ChR2-C128T, ChR2-C128A, and ChR2-C128S were expressed in Xenopus oocytes and recorded photocurrents in response to pulses of 470-nm blue light. Surprisingly, these modifications resulted in dramatic slowing (three to four orders of magnitude) in the closing of the channel after light stimulus was ended. Accordingly, these genes are hereafter referred to as step function opsin (SFO) genes. Compared with the closing time constant of 11.9±0.3 ms for wild-type (wt) ChR2, the time constant for closure after removal of light was measured at 2.0±0.5 s, 52±2 s, and 106±9 s for C128T, C128A, and C128S mutants respectively, revealing vastly extended lifetime of the conducting state (FIG. 1c). As photocurrent amplitudes at a given light intensity are set by a balance between recruitment of new open states and transitions to the closed state, the increased accumulation of the open state was tested for an effectively increased responsiveness at lower light levels. The light intensity dependence of stationary photocurrents was determined by recording responses to light pulses of increasing intensity. The results were normalized to the response at saturating light power (FIG. 1d). Cells expressing C128S and C128A were responsive to light at least 300-fold lower in intensity than those expressing wt ChR2, revealing another surprising property of these SFOs.

Aspects of the present invention include a temporally-precise method of terminating SFO currents. The ChR2 spectral intermediate that reflects the channel open state absorbs maximally at near 520 nm (P520), which is red-shifted relative to the dark state P470. This photo-intermediate can undergo a photoreaction; brief flashes of green light applied during the open state prematurely close the channel. While this photo-intermediate is normally so short-lived that the photochemical back-reaction cannot be efficiently exploited, the extended lifetime of P520 in these C128 mutants allows for the use of green light to flip off the bi-stable switch. Indeed, the inactivation dynamics of C128A and C128S were greatly accelerated when a second light pulse of longer wavelength followed the excitation pulse (FIG. 1e,f). 530 nm light showed highest acceleration of the "off" kinetics, but the current declined to a level far above zero due to significant absorption of this wavelength by the dark state (FIG. 1 e). Light of longer wavelength showed a slower but more complete inactivation due to lower absorption by P480 (improved $\Sigma_{P520}$ to $\Sigma_{P480}$ ratio), and pulses of 546 nm light were found optimal for rapid, complete inactivation. Alternating 450 nm and 546 nm light allowed reversible ON-OFF switching without rundown (FIG. 1f), thereby defining a fast bi-stable switching mechanism for SFOs.

Figure 2A:
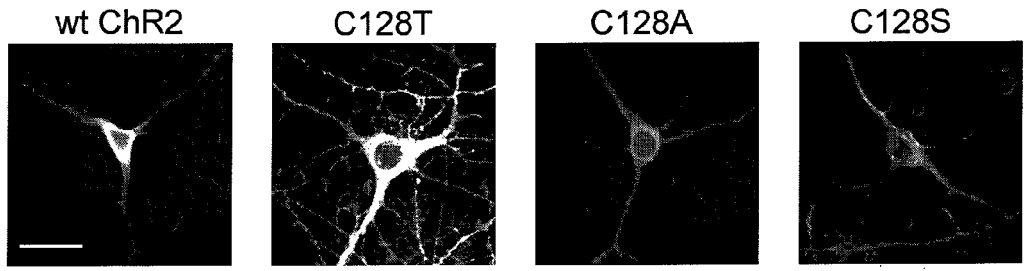
FIG. 2a shows confocal images of cultured hippocampal neurons expressing wt ChR2, C128S, C128A and C128T under the control of the αCaMKII promoter, with intensity scaling and pixel size are identical in all images and scale bar of 25 μm.
Figure 2B:
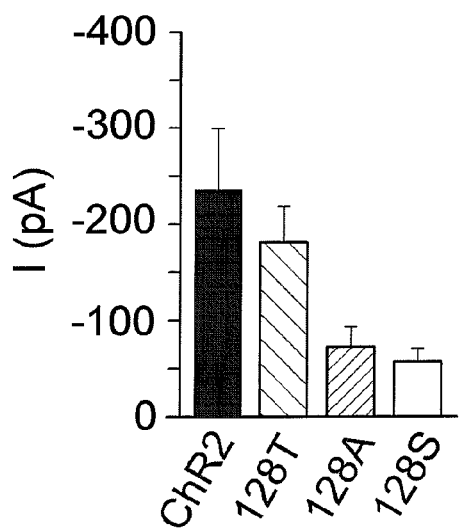
FIG. 2b shows a summary of photocurrents recorded from neurons expressing wt ChR2 and mutants, shown as mean±s.e.m (n=8, 11, 9 and 10 for wt, C128S, C128A and C128T, respectively). Cells were stimulated with a single 10 ms pulse of 470 nm blue light.
Figure 2C:
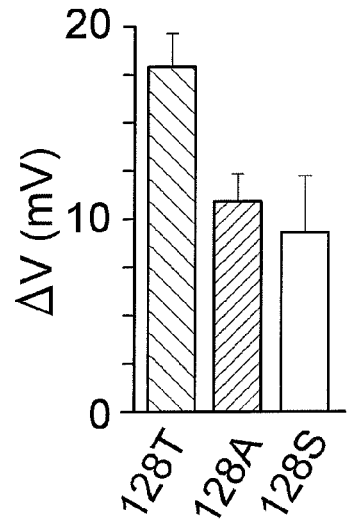
FIG. 2c shows depolarization induced by ChR2 mutants. Voltage recordings were made in neurons expressing C128S, A and T during an identical stimulation protocol as in FIG. 2b. Peak depolarization levels were averaged from 3, 7 and 7 cells for C128S, C128A and C128T, respectively.
Figure 2D:
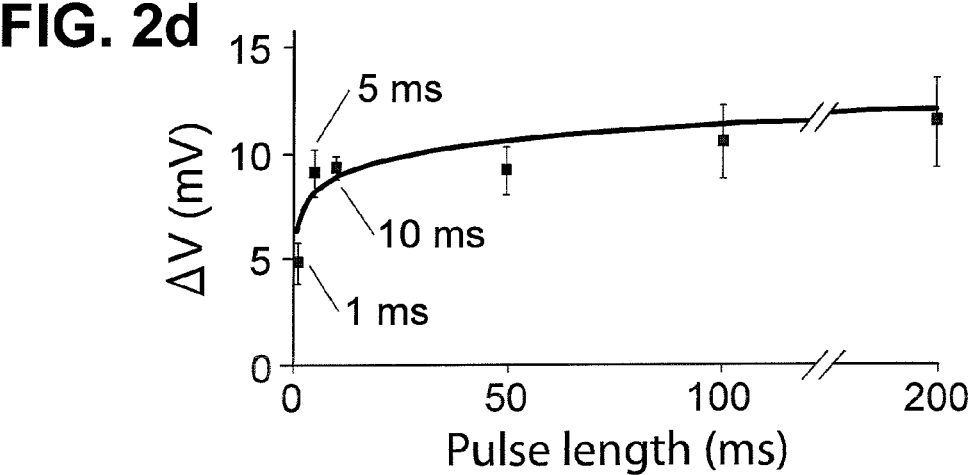
FIG. 2d shows a summary of depolarization in C128A and C128S mutants in response to 470-nm light pulses of varying lengths (data are averaged from at least 3 cells for each pulse length).
Figure 2E:
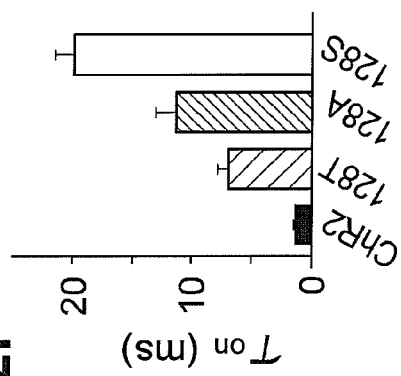
FIG. 2e shows an expanded view of photocurrents evoked by a 10 ms pulse of 470 nm blue light in neurons expressing wt ChR2, C128S, C128A, and C128T, showing slower on-kinetics of the mutants.
Figure 2F:
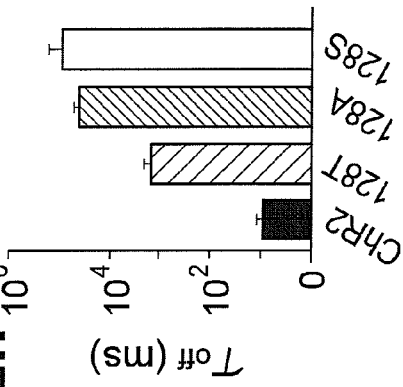
FIG. 2f shows a summary of on-kinetics in response to 10 ms blue light stimulation. Shown are mean time constants from exponential fits to current traces; while onset kinetics of C128S and C128A are similar in FIG. 2e traces, C128S was typically slower than C128A as summarized here.
Figure 2G:
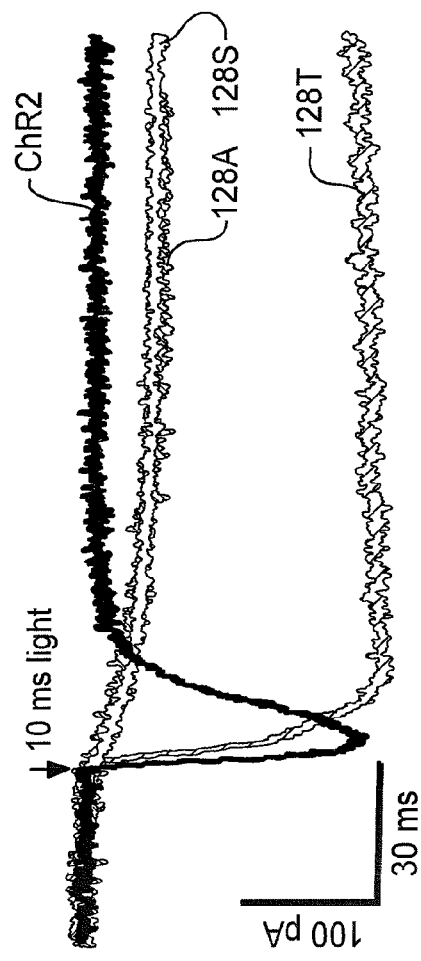
FIG. 2g shows slower decay time constants of photocurrents in the C128 mutants. Traces are normalized to the peak photocurrent in each mutant.
Figure 2H:
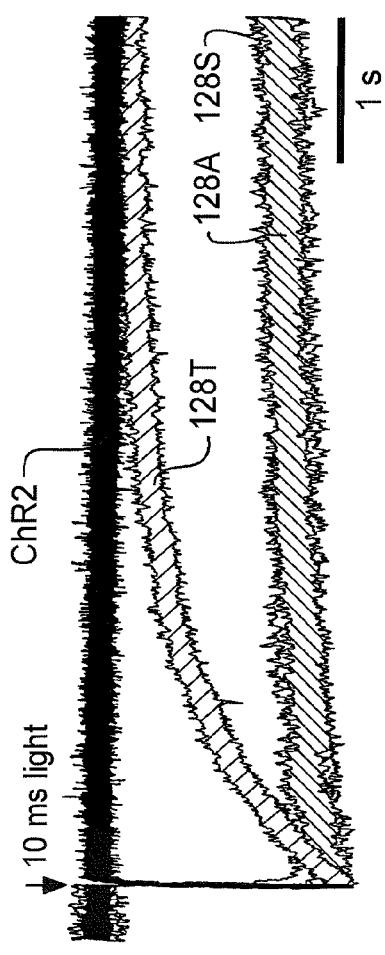
FIG. 2h shows a summary of off-kinetics in C128 mutants. Mean time constants were derived from exponential fits.

This constellation of novel properties represents orders of magnitude advancements in the evolution of the quantitative properties of these channels across multiple dimensions. Many opsins (e.g., Channelopsin-1 or ChR1) do not express in neurons; surprisingly, however, the three SFO genes (C128T, C128A and C128S) were successfully expressed as EYFP-fusions in hippocampal neurons using lentiviral vectors driven by the CaMKIIα promoter. Neurons expressing the three mutants showed sub-cellular distributions similar to that of ChR2-EYFP (FIG. 2a), with C128A and C128S appearing to express at quantitatively reduced levels. Photocurrents evoked by 10 ms pulses of 470 nm light were recorded. Peak photocurrents recorded in C128T were similar to those of wild-type ChR2 (184±34 pA and 240±59 pA respectively; n=10 and 8 cells, respectively; FIG. 2b), whereas C128A and C128S indeed showed smaller photocurrent amplitudes (74±17 pA and 61±9 pA respectively; n=11 and 9 cells, respectively; FIG. 2b). However, brief flashes of up to 10 ms evoked near-maximal currents (FIG. 2b) and voltage changes (FIG. 2c,d) for C128A/S, in all cases, suggesting that the equilibrium of dark state and conducting state is reached within a few milliseconds at a given light intensity. On-kinetics (the response time of channels after a first application of light) in all three mutants remained fast, only slightly slower than wt ChR2 ($\tau_{on}$=1.7±0.1 ms, 11.6±1.5 ms, 7.2±0.8 ms and 20±1.4 ms for ChR2, C128T, C128A and C128S, respectively; FIG. 2f). Corresponding to the oocyte data, mutant photocurrents decayed with up to 4 orders of magnitude slower kinetics after removal of light ($\tau_{off}$=10±0.8 ms, 1.8±0.3 s, 49±3.5 s and 108±42 s, for wt ChR2, C128T, C128A, and C128S, respectively; FIG. 2h). These results show that step-function properties were preserved in neurons.

The capacity of the mutant channels in neurons to elicit prolonged and reversible membrane depolarization in response to short light pulses was tested and the results are depicted in FIG. 3. In neurons expressing C128S, one 10 ms flash of blue light (470 nm) was able to evoke markedly prolonged sub-threshold depolarization (FIG. 3a, top trace), and chronic stimulation protocols consisting of just one 10 ms light pulse every 15 s enabled sustained stable depolarization over minutes that could be rapidly terminated with a single pulse of 535 nm light (FIG. 3a, bottom trace). Indeed, multiple precise steps could be reliably delivered and terminated in the same neurons using pairs of blue and green stimuli (FIG. 3b). Optimal inactivation was found to occur with a 50 ms pulse of 535 nm light (compare top and bottom traces in FIGS. 3b and 3c, consistent with a reduced quantum efficiency for the P520 to P480 transition). Together these data demonstrate bi-stable switching behavior in neurons.

The stable sub-threshold depolarization evoked by photostimulation of C128A or C128S-expressing neurons can be particularly useful for driving precisely timed spike trains (as with WT ChR2), and also for delivering chronically increased excitability, mimicking modulated or UP states (sub-threshold 5-10 mV step-like depolarizations that modulate excitability and information throughput), and for effectively sensitizing genetically-targeted neurons to native, endogenous synaptic inputs. In certain implementations these properties facilitate testing of the causal significance of a neuron type, as neuroscientists often do not know the neural spike code for a particular cell type in executing its function, but could test the causal sufficiency of the cell type by expressing an SFO gene to stably and reversibly enhance natural/intrinsic patterns of information flow through those cells, as illustrated in FIG. 3d.

Figure 3A:
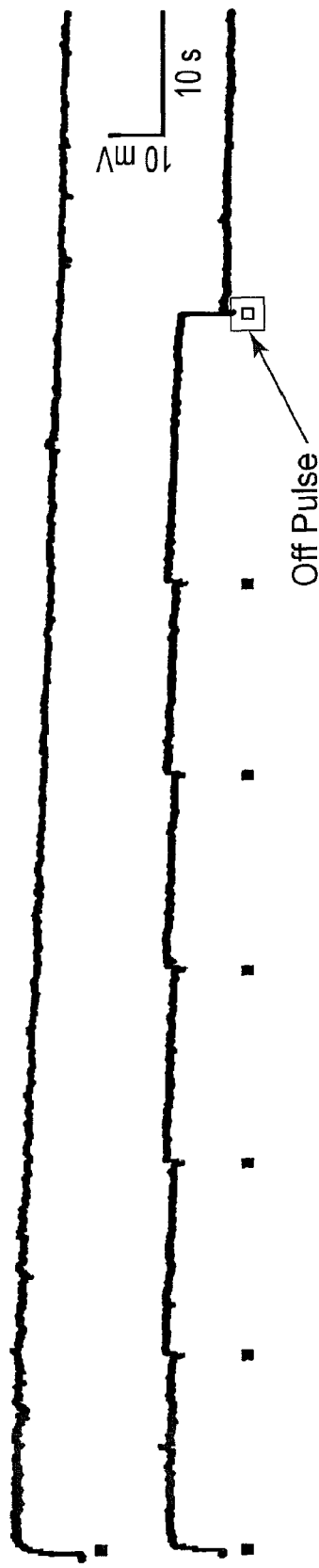
FIG. 3a shows whole-cell current clamp recording from a cultured rat hippocampal neuron expressing C128S under the αCaMKII promoter. Sub-threshold depolarization was induced by a single 10 ms pulse of 470 nm light (top trace; unboxed dash indicates time of stimulus) or by a series of 100 Hz trains consisting of 20 5-ms pulses of 470 nm light (bottom trace, each train is indicated by an unboxed dash, boxed dashes represent green light).
Figure 3C:
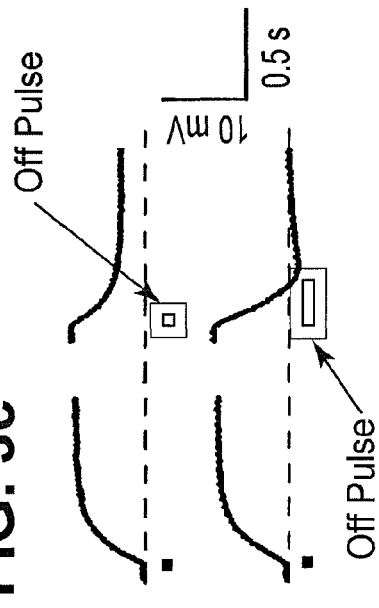
FIG. 3c shows magnified traces from the bottom stimulus pair in FIG. 3b showing complete inactivation with 50 ms green light. Resting membrane potential is indicated by broken line.
Figure 3B:
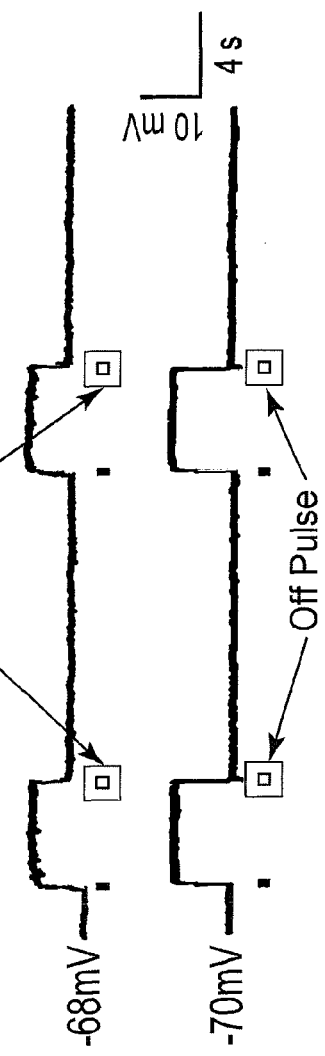
FIG. 3b shows whole-cell current clamp recording from a hippocampal neuron expressing C128S stimulated with pairs of 470- and 535-nm light stimuli. The top trace shows the response to 10 ms blue (unboxed dashes) and 10 ms green light (boxed dashes), and the bottom trace shows the response to 10 ms blue and 50 ms green light. Stimulus pairs were given at 20s intervals, and the interval within each stimulus pair was 5s.
Figure 3D:
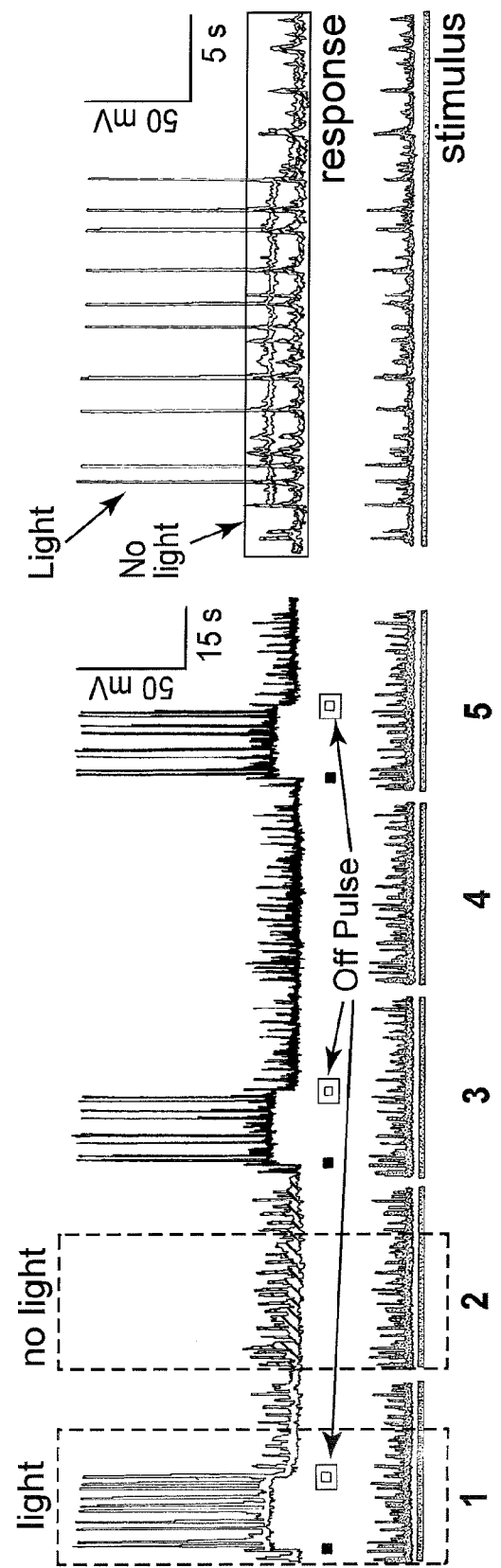
FIG. 3d shows, on the left, whole-cell current clamp recording from a hippocampal neuron expressing C128A stimulated with a pre-recorded EPSP trace.

FIG. 3d shows, on the left, whole-cell current clamp recording from a hippocampal neuron expressing C128A. Native excitatory postsynaptic potential (EPSP) trains were collected with current-clamp recordings in non-transduced hippocampal pyramidal neurons, and the EPSP trains were replayed into cells expressing C128A or C128S before, during and after 20s "UP states" elicited by a blue light pulse (10 ms, 470 nm) and terminated by a green light pulse (50 ms, 535 nm; FIG. 3d). Before or after the UP states, EPSP trains produced little spiking (3±1.1 spikes over 20s), while within UP states the same EPSP train elicited greatly increased spiking (17±3.5 spikes during the 20s period; 9/9 cells increased spiking; p=0.0006, paired t-test). This showed that the SFO genes can be used for neuromodulatory or UP-state-like photo stimulation that sensitizes neurons to ongoing synaptic activity on long timescales that can be precisely defined by an experimenter.

More particularly, the recorded EPSP trace was delivered in 5 identical blocks (lowest two lines). During blocks 1, 3, and 5, pairs of 470 (on pulse)-nm and 535 (off pulse)-nm light stimuli (10 ms and 50 ms, respectively; indicated by boxed and unboxed dashes, respectively) were delivered to induce sub-threshold depolarization. During blocks 2 and 4, no light was delivered. On the right, FIG. 3d shows a magnification of response to EPSPs with and without light (overlay of dashed black boxes) shows light-induced increase in spiking to EPSP stimuli (bottom trace).

The C128A and C128S probes provide properties useful for manipulating neuronal circuits. In addition to allowing novel basic science applications, reduced light requirements are particularly useful with regard to optical hardware requirements in preclinical and clinical experiments, reducing power draw, heating, and risks for long-term photo toxicity. Additional enhancements include red-shifted VChR1 versions for recruiting larger volumes of tissue with lower-energy photons, and molecular modifications to increase membrane trafficking as with eNpHR. Multiple orders of magnitude improvement in both stability and light responsiveness, coupled with precise on/off switching and the chemical cofactor independence of channelrhodopsins, together offer a constellation of key properties for both basic and preclinical/clinical research into mammalian neural circuitry.

Embodiments of the present invention include modifications of other portions of ChR2. Characterization of the properties can be carried out as discussed above. For example, modifications made in the vicinity of C128 are within the scope of the present invention. Other possibilities include, but are not limited to, modifications to, or in the vicinity of, E123 and H134 alone or in combination with modifications at or near C128.

A particular implementation relates to a mutation H134R with the mutations C128A or C128T. It has been discovered that these mutations enhance the conductance, while also providing time constants consistent with those mentioned herein mutants (42 seconds for C128A and 2.5 seconds for C128T). As shown in FIG. 4c, the current sizes are larger and thus can be particularly useful for depolarizing neurons past the threshold for spiking. Also depicted in FIG. 4c are turn on times (top right), turn-off times without light (bottom left), and turn-off times in response to light (bottom right).

Figure 5:
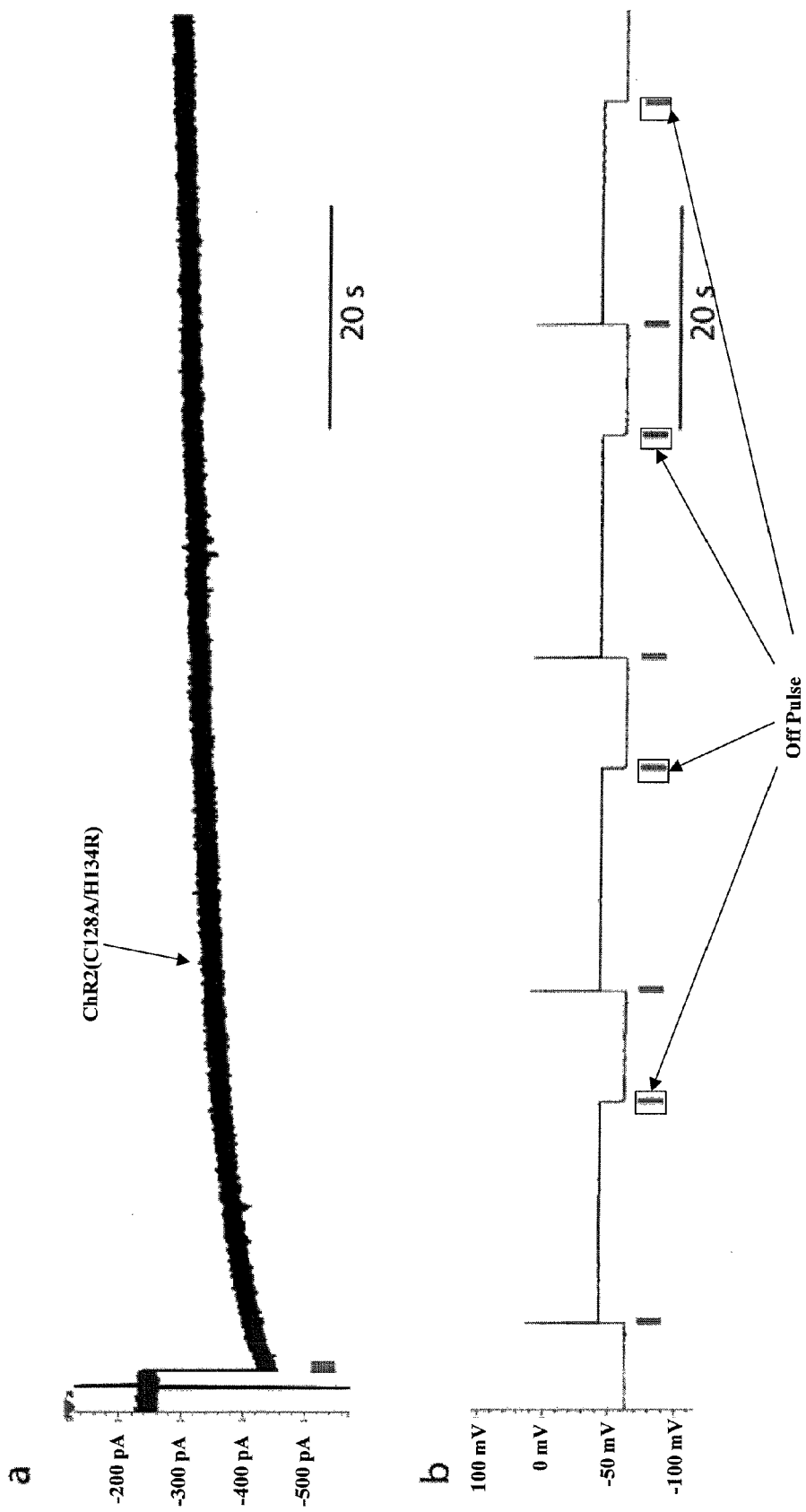
FIG. 5a shows current recording from a cell expressing ChR2 (C128A/H134R) and particularly a 200 pA photocurrent in response to a 10 ms on/blue light pulse, decaying slowly to baseline.
FIG. 5b shows a voltage recording from the same cell as in FIG. 5a, showing the response of the cell to repeated delivery of pairs of 10 ms 470 nm light (on/blue pulses) and 100 ms 560 nm light (off/green pulses).

FIG. 5 shows sample currents recorded from cells expressing ChR2 (C128A/H134R), also showing spiking in response to activation of this mutant. FIG. 5a shows current recording from a cell expressing ChR2 (C128A/H134R) and particularly a 200 pA photocurrent in response to a 10 ms on/blue light pulse, decaying slowly to baseline. FIG. 5b shows a voltage recording from the same cell as in FIG. 5a, showing the response of the cell to repeated delivery of pairs of 10 ms 470 nm light (on/blue pulses) and 100 ms 560 nm light (off/green pulses).

Embodiments of the present invention are directed to modifications of ChR1 or VChR1. As shown in FIG. 1a, the modifications can be made to locations that are homologous to those discussed in connection with ChR2. For instance, a modification is made to C123 of VChR1 that includes substitution by one of with Thr, Ala or Ser.

Figure 6:
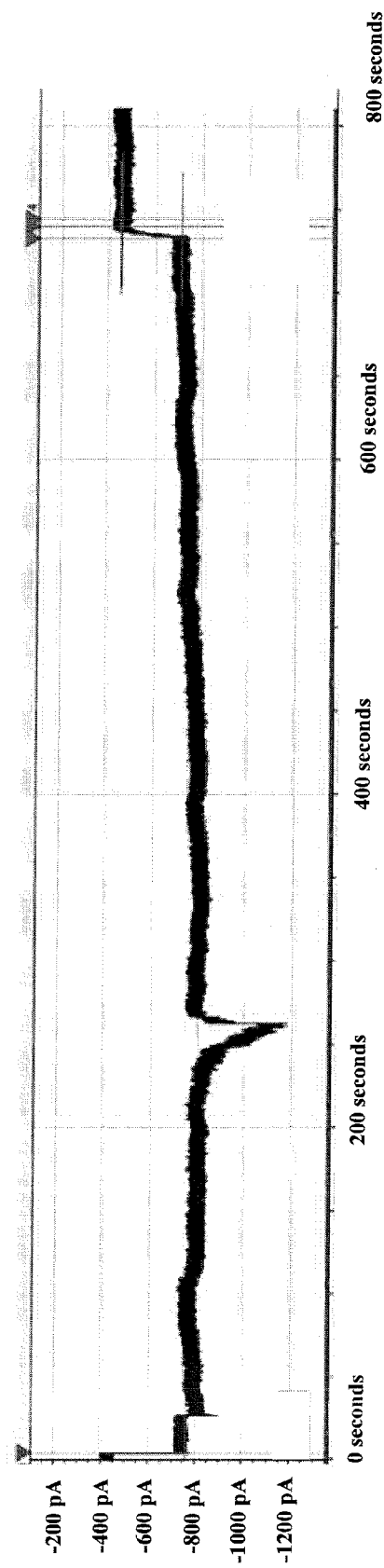
FIG. 6 shows a current recording in a cell expressing ChR2 (C128S/D156A) showing the slow kinetics in response to an on-pulse.

Consistent with another embodiment of the present invention, modifications/substitutions are made to ChR2 at or near D156. For instance, experimental results have shown that double mutant C128S/D156A has slow closure kinetics. In recordings from cells in culture, the current triggered by a single 10 ms flash of blue light only decayed to ~90% of its initial size after 13 minutes of recording (FIG. 6). The light sensitivity of this mutant is superior to all previously tested SFOs and it can respond with maximal photocurrent down to 1 μW/mm2 of light.

Other embodiments of the present invention include a similar mutation(s) to VChR1 at for creating a similarly slow, yet red-shifted, channel (e.g., C123S/D151A). For instance, a C123S substitution in VChR1 results in a surprising step-function opsin having a time constant of channel closure after removal of light that is around 30s (FIG. 4c) relative to unmodified VChR1, which is on the order of 120 ms.

Figure 4A:
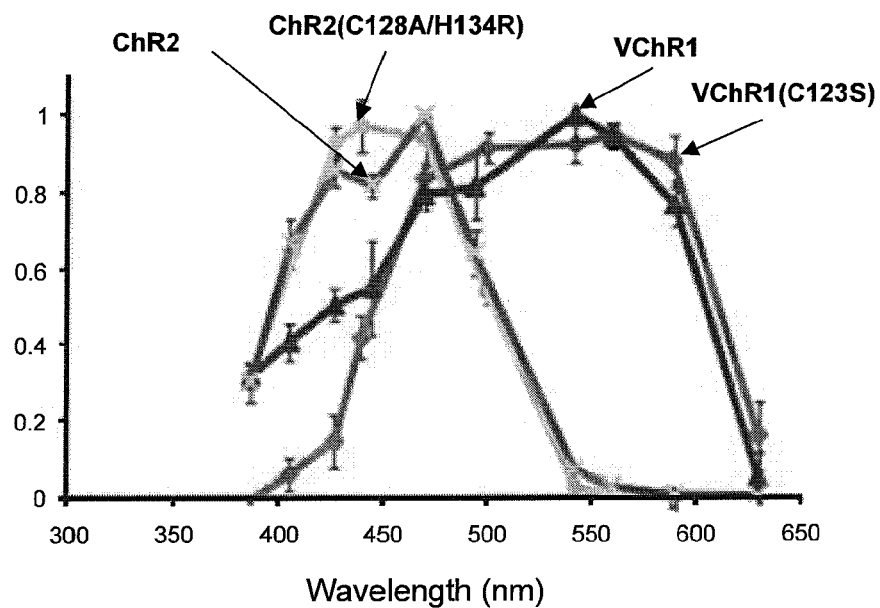
FIG. 4a shows excitation spectra for ChR2, ChR2 (C128A/H134R), VChR1 and VChR1 (C123S), and more particularly.
Figure 4B:
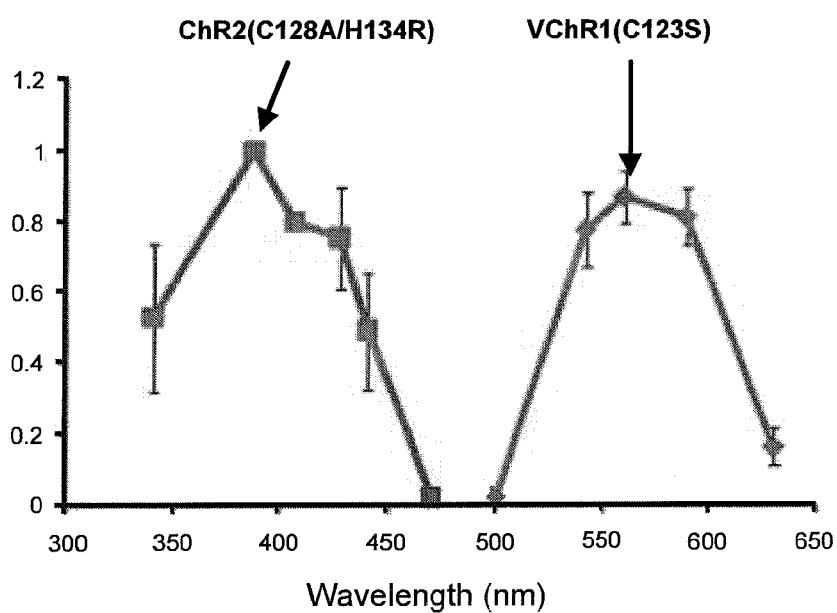
FIG. 4b shows that ChR2 (C128A/H134R) maintains a shifted spectra relative to VChR1 (C123S).
Figure 4C:
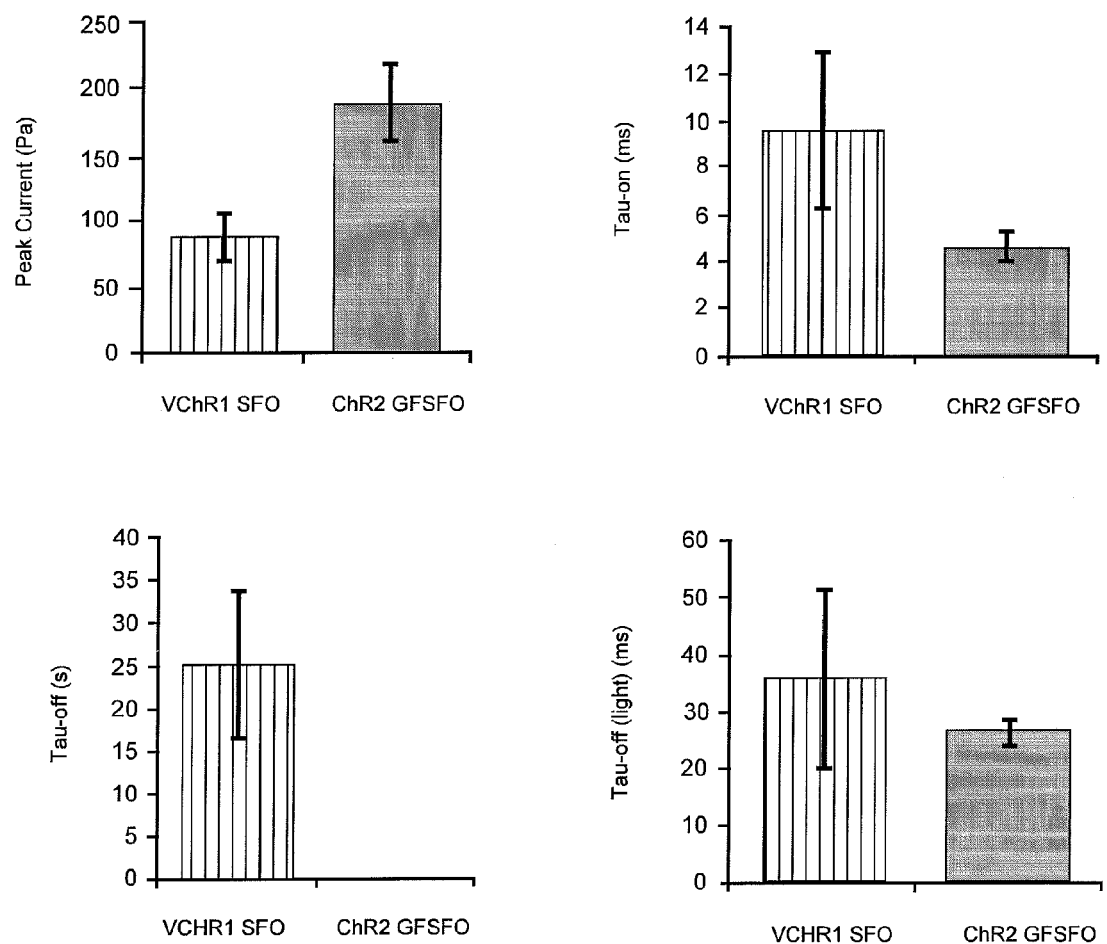
FIG. 4c shows peak current size and on- and off-kinetics (e.g., the time from the initial light the corresponding (de)activation of the channels) for VChR1 SFO and ChR2 gain-of-function (GF) SFO (C128A/H134R).

Aspects of the present invention relate to the use of the red-shifted (relative to ChR2) excitation of VChR1 (FIG. 4a). The red-shift can be particularly useful for deep tissue penetration in connection with the relatively long time constant. For instance, using a step-function version of VChR1, light can be delivered at both a low intensity and repetition rate to achieve chronic activation of targeted cells. Another aspect relates to the spectral separation from ChR2 and the ChR2-based SFOs (FIG. 4a, 4b). For instance, modified VChR1 can be expressed in a first neuronal population while modified ChR2 can be expressed in another neuronal population. Different wavelengths of stimulus light can thereby allow dual-channel control of excitability in the two different neuronal populations.

FIG. 6 shows long current recording of ChR2 mutant C128S/D156A, consistent with an embodiment of the present invention. As shown here, the mutant provides slow closure kinetics relative to non-mutated ChR2 and similar light-responsive channels.

Embodiments of the present invention lend themselves to a wide range of applications. A few exemplary applications are discussed hereafter, however, the invention is not limited to these specific examples. Instead, the examples present examples of implementations and show that aspects of the present invention lend themselves to broad range of applications.

One such application relates to facilitation of intrinsic action potential generation in neural cells for extended periods of time and with high temporal precision. As supported by the various experimental results, certain SFOs allow for rapid on/off control with bi-stable characteristics. Intrinsic neural stimulation produces action potentials in a neuron when the stimulation is sufficient to overcome the resting potential of the neuron. A neural population engineered to express such SFOs provides optical control of this resting potential, thereby facilitating action potentials as a result of a naturally-occurring stimulus. This control can be facilitated by the recognition that certain SFOs have fast-temporal responsiveness that persists over a long-time period. For instance, activation (conductive response) of the SFOs can be on the order of milliseconds after the application of an optical stimulus, while the SFOs can also remain activated for hundreds of milliseconds or even hundreds of seconds after the optical stimulus have been removed. This can be particularly useful for precise control over SFO activation while reducing the amount of potentially-detrimental (e.g., cell health, optically generated heat and/or battery power drain) optical stimulus necessary to maintain SFO activation. Moreover, various SFOs have shown relative fast temporal off-times when exposed to light of a particular wavelength. Thus, precise temporal control can be accomplished with minimal optical stimulation, while facilitating intrinsic activity of neural cells or populations.

Consistent with a more specific example embodiment of the present invention an additional molecule, such as NpHR from *Natronomonas pharaonis*, can be used for temporally-precise optical inhibition of neural activity. NpHR allows for selective inhibition of single action potentials within rapid spike trains and sustained blockade of spiking over many minutes. The action spectrum of NpHR is strongly red-shifted relative to ChannelRhodopsin-2 (ChR2) (derived from *Chlamydomonas reinhardtii*) but operates at similar light power, and NpHR functions in mammals without exogenous cofactors. In one instance, both NpHR and ChR2 can be expressed in the target cells. Likewise, NpHR and ChR2 can be targeted to *C. elegans* muscle and cholinergic motoneurons to control locomotion bi-directionally. In this regard, NpHR and ChR2 form an optogenetic system for multimodal, high-speed, genetically-targeted, all-optical interrogation of living neural circuits.

According to other example embodiments of the present invention, methods for generating an inhibitory neuron-current flow involve, in a neuron, engineering a protein that responds to light by producing an inhibitory current to dissuade depolarization of the neuron. In one such method, the protein is halorhodopsin-based and in another method the protein is an inhibitory protein that uses an endogenous cofactor.

In another example embodiment, a method for controlling action potential of a neuron involves the following steps: engineering a first light responsive protein in the neuron; producing, in response to light, an inhibitory current in the neuron and from the first light responsive protein; engineering a second light responsive protein in the neuron; and producing, in response to light, an excitation current in the neuron from the second light responsive protein.

Another embodiment involves method for controlling a voltage level across a cell membrane of a cell, the method includes: engineering a first light responsive protein in the cell; measuring the voltage level across the cell membrane; and producing, in response to light of a first wavelength and using the first light responsive protein, a current across the cell membrane that is responsive to the measured voltage level.

Another aspect of the present invention is directed to a system for controlling an action potential of a neuron in vivo. The system includes a delivery device, a light source, and a control device. The delivery device introduces a light responsive protein to the neuron, with the light responsive protein producing an inhibitory current. The light source generates light for stimulating the light responsive protein, and the control device controls the generation of light by the light source.

In more detailed embodiments, such a system is further adapted such that the delivery device introduces the light responsive protein by one of transfection, transduction and microinjection, and/or such that the light source introduces light to the neuron via one of an implantable light generator and fiber-optics.

Specific aspects of the present invention are directed toward the use of an archaeal light-driven chloride pump, such as halorhodopsin (NpHR), from *Natronomonas pharaonis*, for temporally-precise optical inhibition of neural activity. NpHR-based pumps allow both knockout of single action potentials within rapid spike trains and sustained blockade of spiking over many minutes, and operate at similar light power compared to SFOs based upon ChR2 or VChR1 but with a strongly red-shifted action spectrum. The NpHR pump also functions in mammals without exogenous cofactors.

More detailed embodiments expand on such techniques. For instance, another aspect of the present invention co-expresses NpHR and SFOs (e.g., ChR2 or VChr1 variants) in the species (e.g., a mouse and *C. elegans*). Also, NpHR and SFOs are integrated with calcium imaging in acute mammalian brain slices for bidirectional optical modulation and readout of neural activity. Likewise, NpHR and SFOs can be targeted to *C. elegans* muscle and cholinergic motoneurons to provide bidirectional control of locomotion. Together NpHR and SFOs can be used as a complete and complementary optogenetic system for multimodal, high-speed, genetically-targeted, all-optical interrogation of living neural circuits.

In addition to variants of NpHR, ChR2 and VChR1, there are a number of channelrhodopsins, halorhodopsins, and microbial opsins that can be engineered to optically regulate ion flux or second messengers within cells. Various embodiments of the invention include codon-optimized, mutated, truncated, fusion proteins, targeted versions, or otherwise modified versions of such ion optical regulators. Thus, ChR2 and NpHR (e.g., GenBank accession number is EF474018 for the 'mammalianized' NpHR sequence and EF474017 for the 'mammalianized' ChR2(1-315) sequence), and variants, are used as representative of a number of different embodiments. Discussions specifically identifying SFOs, ChR2 and NpHR are not meant to limit the invention to such specific examples of optical regulators. For further details regarding the above mentioned sequences reference can be made to "Multimodal fast optical interrogation of neural circuitry" by Feng Zhang, et al, Nature (Apr. 5, 2007) Vol. 446: 633-639, which is fully incorporated herein by reference. As discussed herein, these sequences can be modified accordingly to provide the desired channel kinetics.

Consistent with an example embodiment of the present invention, a method is implemented for stimulating target cells in vivo using gene transfer vectors (for example, viruses) capable of inducing photosensitive ion channel growth (for example, SFO/ChR2-based ion channels). The vectors can be implanted in the body.

Consistent with a particular embodiment of the present invention, a protein is introduced to one or more target cells. When introduced into a cell, the protein changes the potential of the cell in response to light having a certain frequency. This may result in a change in resting potential that can be used to control (dissuade) action potential firing. In a specific example, the protein is a halorhodopsin that acts as a membrane pump for transferring charge across the cell membrane in response to light, Membrane pumps are energy transducers which use electromagnetic or chemical bond energy for translocation of specific ions across the membrane. For further information regarding halorhodopsin membrane pumps reference can be made to "Halorhodopsin Is a Light-driven Chloride Pump" by Brigitte Schobert, et al, The Journal of Biological Chemistry Vol. 257, No. 17. Sep. 10, 1982, pp. 10306-10313, which is fully incorporated herein by reference.

The protein dissuades firing of the action potential by moving the potential of the cell away from the action potential trigger level for the cell. In many neurons, this means that the protein increases the negative voltage seen across the cell membrane. In a specific instance, the protein acts as a chloride ion pump that actively transfers negatively charged chloride ions into the cell. In this manner, the protein generates an inhibitory current across the cell membrane. More specifically, the protein responds to light by lowering the voltage across the cell thereby decreasing the probability that an action potential or depolarization will occur.

As discussed above, one embodiment of the present invention involves the use of an optically responsive ion-pump that is expressed in a cell. In a particular instance, the cell is either a neural cell or a stem cell. A specific embodiment involves in vivo animal cells expressing the ion-pump. Certain aspects of the present invention are based on the identification and development of an archaeal light-driven chloride pump, such as halorhodopsin derived from *Natronomonas pharaonis* (NpHR), for temporally-precise optical inhibition of neural activity. The pump allows both knockout of single action potentials within rapid spike trains and sustained blockade of spiking over many minutes, and it operates at similar light power compared to ChR2-based variants but with a strongly red-shifted action spectrum. The NpHR pump also functions in mammals without exogenous cofactors.

According to an example embodiment of the present invention, an optically responsive ion-pump and/or channel is expressed in one or more stem cells, progenitor cells, or progeny of stem or progenitor cells. Optical stimulation is used to activate expressed pumps/channels. The activation can be used to control the ion concentrations (e.g., chloride, calcium, sodium, and potassium) in the cells. This can be particularly useful for affecting the survival, proliferation, differentiation, de-differentiation, or lack of differentiation in the cells. Thus, optical stimulus is implemented to provide control over the (maturation) of stem or progenitor cells.

In a particular embodiment, optically-controlled stimulus patterns are applied to the stem or progenitor cells over a period of hours or days. For further details regarding the effects of membrane potentials and ion concentrations on such cells reference can be made to "Excitation-Neurogenesis Coupling in Adult Neural Stem/Progenitor Cells" by Karl Deisseroth, et al, Neuron (May 27, 2004) Neuron, Vol. 42, 535-552 and to U.S. Patent Publication No. 20050267011 (U.S. patent application Ser. No. 11/134,720) entitled "Coupling of Excitation and Neurogenesis in Neural Stem/Progenitor Cells" to Deisseroth et al and filed on May 19, 2005, which are each fully incorporated herein by reference.

In a particular embodiment, a method of driving differentiation in cells is implemented. The cells are caused to express light-activated NpHR/ChR2-based proteins. The cells are exposed to light to activate the NpHR/ChR2-based protein. The activation drives differentiation of the exposed cell or the progeny of the exposed cell. In another embodiment, the cells comprise stem cells.

Other embodiments relate to aspects of the present invention that are directed to a method for treatment/assessment of a disorder or circuit model. One such method uses SFOs and (possibly) inhibitory molecules to selectively encourage or inhibit neurons. The method targets a group of neurons associated with the disorder; and in this group, the method includes engineering an inhibitory protein/molecule that uses an endogenous cofactor to respond to light by producing an inhibitory current to dissuade depolarization of the neurons. The method also includes engineering SFOs in neurons, of the same group and/or of a different group. The engineered neurons are then exposed to light, thereby dissuading and/or encouraging depolarization of the neurons. The putative effects of this stimulation are then monitored and assessed. Different stimulation profiles and/or targeted locations can be implemented, tested and assessed. The various properties (e.g., the bi-stable nature and fast responsiveness) of SFOs can be particularly useful for such applications, some of which are discussed in more detail hereafter.

Many human applications of the present invention require governmental approval prior to their use. For instance, human use of gene therapy may require such approval. However, similar gene therapies in neurons (nonproliferative cells that are non-susceptible to neoplasms) are proceeding rapidly, with active, FDA-approved clinical trials already underway involving viral gene delivery to human brains thereby facilitating the use of various embodiments of the present invention for a large variety of applications. The following is a non-exhaustive list of a few examples of such applications and embodiments.

Addiction is associated with a variety of brain functions, including reward and expectation. Additionally, the driving cause of addiction may vary between individuals. According to one embodiment, addiction, for example nicotine addiction, may be treated with optogenetic stabilization of small areas on the insula. Optionally, functional brain imaging—for example cued-state PET or fMRI—may be used to locate a hypermetabolic focus in order to determine a precise target spot for the intervention on the insula surface.

Optogenetic excitation of the nucleus accumbens and septum may provide reward and pleasure to a patient without need for resorting to use of substances, and hence may hold a key to addiction treatment. Conversely, optogenetic stabilization of the nucleus accumbens and septum may be used to decrease drug craving in the context of addiction. In an alternative embodiment, optogenetic stabilization of hypermetabolic activity observed at the genu of the anterior cingulate (BA32) can be used to decrease drug craving. Optogenetic stabilization of cells within the arcuate nucleus of the medial hypothalamus which contain peptide products of proopiomelanocortin (POMC) and cocaine-and-amphetamine-regulating transcript (CART) can also be used to decrease drug addiction behavior. For further information in this regard, reference may be made to: Naqvi N H, Rudrauf D, Damasio H, Bechara A. "Damage to the insula disrupts addiction to cigarette smoking." Science. 2007 Jan. 26; 315(5811):531-534, which is fully incorporated herein by reference.

Optogenetic stimulation of neuroendocrine neurons of the hypothalamic periventricular nucleus that secrete somatostatin can be used to inhibit secretion of growth hormone from the anterior pituitary, for example in acromegaly. Optogenetic stabilization of neuroendocrine neurons that secrete somatostatin or growth hormone can be used to increase growth and physical development. Among the changes that accompany "normal" aging, is a sharp decline in serum growth hormone levels after the 4$^{th}$ and 5$^{th}$ decades. Consequently, physical deterioration associated with aging may be lessened through optogenetic stabilization of the periventricular nucleus.

Optogenetic stabilization of the ventromedial nucleus of the hypothalamus, particularly the proopiomelanocortin (POMC) and cocaine-and-amphetamine-regulating transcript (CART) of the arcuate nucleus, can be used to increase appetite, and thereby treat anorexia nervosa. Alternatively, optogenetic stimulation of the lateral nuclei of the hypothalamus can be used to increase appetite and eating behaviors.

Optogenetic excitation in the cholinergic cells of affected areas including the temporal lobe, the NBM (Nucleus basalis of Meynert) and the posterior cingulate gyrus (BA 31) provides stimulation, and hence neurotrophic drive to deteriorating areas. Because the affected areas are widespread within the brain, an analogous treatment with implanted electrodes may be less feasible than an optogenetic approach.

Anxiety disorders are typically associated with increased activity in the left temporal and frontal cortex and amygdala, which trends toward normal as anxiety resolves. Accordingly, the affected left temporal and frontal regions and amygdala may be treated with optogenetic stabilization, so as to dampen activity in these regions.

In normal physiology, photosensitive neural cells of the retina, which depolarize in response to the light that they receive, create a visual map of the received light pattern. Optogenetic ion channels can be used to mimic this process in many parts of the body, and the eyes are no exception. In the case of visual impairment or blindness due to damaged retina, a functionally new retina can be grown, which uses natural ambient light rather than flashing light patterns from an implanted device. The artificial retina grown may be placed in the location of the original retina (where it can take advantage of the optic nerve serving as a conduit back to the visual cortex). Alternatively, the artificial retina may be placed in another location, such as the forehead, provided that a conduit for the depolarization signals are transmitted to cortical tissue capable of deciphering the encoded information from the optogenetic sensor matrix. Cortical blindness could also be treated by simulating visual pathways downstream of the visual cortex. The stimulation would be based on visual data produced up stream of the visual cortex or by an artificial light sensor.

Treatment of tachycardia may be accomplished with optogenetic stimulation to parasympathetic nervous system fibers including CN X or Vagus Nerve. This causes a decrease in the SA node rate, thereby decreasing the heart rate and force of contraction. Similarly, optogenetic stabilization of sympathetic nervous system fibers within spinal nerves T1 through T4, serves to slow the heart. For the treatment of pathological bradycardia, optogenetic stabilization of the Vagus nerve, or optogenetic stimulation of sympathetic fibers in T1 through T4 will serve to increase heart rate. Cardiac dysrhythmias resulting from aberrant electrical foci that outpace the sinoatrial node may be suppressed by treating the aberrant electrical focus with moderate optogenetic stabilization. This decreases the intrinsic rate of firing within the treated tissue, and permits the sinoatrial node to regain its role in pacing the heart's electrical system. In a similar way, any type of cardiac arrhythmia could be treated. Degeneration of cardiac tissue that occurs in cardiomyopathy or congestive heart failure could also be treated using this invention; the remaining tissue could be excited using various embodiments of the invention.

Optogenetic excitation stimulation of brain regions including the frontal lobe, parietal lobes and hippocampi, may increase processing speed, improve memory, and stimulate growth and interconnection of neurons, including spurring development of neural progenitor cells. As an example, one such application of the present invention is directed to optogenetic excitation stimulation of targeted neurons in the thalamus for the purpose of bringing a patient out of a near-vegetative (barely-conscious) state. Growth of light-gated ion channels or pumps in the membrane of targeted thalamus neurons is effected. These modified neurons are then stimulated, e.g., via optics which may also gain access by the same passageway, by directing a flash of light thereupon so as to modulate the function of the targeted neurons and/or surrounding cells. For further information regarding appropriate modulation techniques (via electrode-based treatment) or further information regarding the associated brain regions for such patients, reference may be made to: Schiff N D, Giacino J T, Kalmar K, Victor J D, Baker K, Gerber M, Fritz B, Eisenberg B, O'Connor J O, Kobylarz E J, Farris S, Machado A, McCagg C, Plum F, Fins J J, Rezai A R. "Behavioral improvements with thalamic stimulation after severe traumatic brain injury." Nature. Vol 448. Aug. 2, 2007 pp 600-604.

In an alternative embodiment, optogenetic excitation may be used to treat weakened cardiac muscle in conditions such as congestive heart failure. Electrical assistance to failing heart muscle of CHF is generally not practical, due to the thin-stretched, fragile state of the cardiac wall, and the difficulty in providing an evenly distributed electrical coupling between an electrodes and muscle. For this reason, preferred methods to date for increasing cardiac contractility have involved either pharmacological methods such as Beta agonists, and mechanical approaches such as ventricular assist devices. In this embodiment of the present invention, optogenetic excitation is delivered to weakened heart muscle via light emitting elements on the inner surface of a jacket surround the heart or otherwise against the affected heart wall. Light may be diffused by means well known in the art, to smoothly cover large areas of muscle, prompting contraction with each light pulse.

Optogenetic stabilization in the subgenual portion of the cingulate gyms (Cg25), yellow light may be applied with an implanted device to treat depression by suppressing target activity in manner analogous to what is taught by Mayberg H S et al., "Deep Brain Stimulation for Treatment-Resistant Depression." Neuron, Vol. 45, 651-660, Mar. 3, 2005, 651-660, which is fully incorporated herein by reference. In an alternative embodiment, an optogenetic excitation stimulation method is to increase activity in that region in a manner analogous to what is taught by Schlaepfer et al., "Deep Brain stimulation to Reward Circuitry Alleviates Anhedonia in Refractory Major Depression." Neuropsychopharmacology 2007 1-10, which is fully incorporated herein by reference. In yet another embodiment the left dorsolateral prefrontal cortex (LDPFC) is targeted with an optogenetic excitation stimulation method. Pacing the LDLPFC at 5-20 Hz serves to increase the basal metabolic level of this structure which, via connecting circuitry, serves to decrease activity in Cg 25, improving depression in the process. Suppression of the right dorsolateral prefrontal cortex (RDLPFC) is also an effective depression treatment strategy. This may be accomplished by optogenetic stabilization on the RDLPFC, or suppression may also be accomplished by using optogenetic excitation stimulation, and pulsing at a slow rate—1 Hz or less, improving depression in the process. Vagus nerve stimulation (VNS) may be improved using an optogenetic approach. Use of optogenetic excitation may be used in order to stimulate only the vagus afferents to the brain, such as the nodose ganglion and the jugular ganglion. Efferents from the brain would not receive stimulation by this approach, thus eliminating some of the side-effects of VNS including discomfort in the throat, a cough, difficulty swallowing and a hoarse voice. In an alternative embodiment, the hippocampus may be optogenetically excited, leading to increased dendritic and axonal sprouting, and overall growth of the hippocampus. Other brain regions implicated in depression that could be treated using this invention include the amygdala, accumbens, orbitofrontal and orbitomedial cortex, hippocampus, olfactory cortex, and dopaminergic, serotonergic, and noradrenergic projections. Optogenetic approaches could be used to control spread of activity through structures like the hippocampus to control depressive symptoms.

So long as there are viable alpha and beta cell populations in the pancreatic islets of Langerhans, the islets can be targeted for the treatment of diabetes. For example, when serum glucose is high (as determined manually or by closed loop glucose detection system), optogenetic excitation may be used to cause insulin release from the beta cells of the islets of Langerhans in the pancreas, while optogenetic stabilization is used to prevent glucagon release from the alpha cells of the islets of Langerhans in the pancreas. Conversely, when blood sugars are too low (as determined manually or by closed loop glucose detection system), optogenetic stabilization may be used to stop beta cell secretion of insulin, and optogenetic excitation may be used to increase alpha-cell secretion of glucagon.

For treatment of epilepsy, quenching or blocking epileptogenic activity is amenable to optogenetic approaches. Most epilepsy patients have a stereotyped pattern of activity spread resulting from an epileptogenic focus. Optogenetic stabilization could be used to suppress the abnormal activity before it spreads or truncated it early in its course. Alternatively, activation of excitatory tissue via optogenetic excitation stimulation could be delivered in a series of deliberately asynchronous patterns to disrupt the emerging seizure activity. Another alternative involves the activation of optogenetic excitation stimulation in GABAergic neurons to provide a similar result. Thalamic relays may be targeted with optogenetic stabilization triggered when an abnormal EEG pattern is detected.

Another embodiment involves the treatment of gastrointestinal disorders. The digestive system has its own, semi-autonomous nervous system containing sensory neurons, motor neurons and interneurons. These neurons control movement of the GI tract, as well as trigger specific cells in the gut to release acid, digestive enzymes, and hormones including gastrin, cholecystokinin and secretin. Syndromes that include inadequate secretion of any of these cellular products may be treated with optogenetic stimulation of the producing cell types, or neurons that prompt their activity. Conversely, optogenetic stabilization may be used to treat syndromes in which excessive endocrine and exocrine products are being created. Disorders of lowered intestinal motility, ranging from constipation (particularly in patients with spinal cord injury) to megacolon may be treated with optogenetic excitation of motor neurons in the intestines. Disorders of intestinal hypermotility, including some forms of irritable bowel syndrome may be treated with optogenetic stabilization of neurons that control motility. Neurogenetic gastric outlet obstructions may be treated with optogenetic stabilization of neurons and musculature in the pyloris. An alternative approach to hypomobility syndromes would be to provide optogenetic excitation to stretch-sensitive neurons in the walls of the gut, increasing the signal that the gut is full and in need of emptying.

In this same paradigm, an approach to hypermobility syndromes of the gut would be to provide optogenetic stabilization to stretch receptor neurons in the lower GI, thus providing a "false cue" that the gut was empty, and not in need of emptying. In the case of frank fecal incontinence, gaining improved control of the internal and external sphincters may be preferred to slowing the motility of the entire tract. During periods of time during which a patient needs to hold feces in, optogenetic excitation of the internal anal sphincter will provide for retention. Providing optogenetic stimulation to the external sphincter may be used to provide additional continence. When the patient is required to defecate, the internal anal sphincter, and then external anal sphincter should be relaxed, either by pausing the optogenetic stimulation, or by adding optogenetic stabilization.

Conductive hearing loss may be treated by the use of optical cochlear implants. Once the cochlea has been prepared for optogenetic stimulation, a cochlear implant that flashes light may be used. Sensorineural hearing loss may be treated through optical stimulation of downstream targets in the auditory pathway.

Another embodiment of the present invention is directed toward the treatment of blood pressure disorders, such as hypertension. Baroreceptors and chemoreceptors in regions such as the aorta (aortic bodies and paraaortic bodies) and the carotid arteries ("carotid bodies") participate the regulation of blood pressure and respiration by sending afferents via the vagus nerve (CN X), and other pathways to the medulla and pons, particularly the solitary tract and nucleus. Optogenetic excitation of the carotid bodies, aortic bodies, paraaortic bodies, may be used to send a false message of "hypertension" to the solitary nucleus and tract, causing it to report that blood pressure should be decreased. Optogenetic excitation or stabilization directly to appropriate parts of the brainstem may also be used to lower blood pressure. The opposite modality causes the optogenetic approach to serve as a pressor, raising blood pressure. A similar effect may also be achieved via optogenetic excitation of the Vagus nerve, or by optogenetic stabilization of sympathetic fibers within spinal nerves T1-T4. In an alternative embodiment, hypertension may be treated with optogenetic stabilization of the heart, resulting in decreased cardiac output and lowered blood pressure. According to another embodiment, optogenetic stabilization of aldosterone-producing cells within the adrenal cortex may be used to decrease blood pressure. In yet another alternative embodiment, hypertension may be treated by optogenetic stabilization of vascular smooth muscle. Activating light may be passed transcutaneously to the peripheral vascular bed.

Another example embodiment is directed toward the treatment of hypothalamic-pituitary-adrenal axis disorders. In the treatment of hypothyroidism, optogenetic excitation of parvocellular neuroendocrine, neurons in the paraventricular and anterior hypothalamic nuclei can be used to increase secretion of thyrotropin-releasing hormone (TRH). TRH, in turn, stimulates anterior pituitary to secrete thyroid stimulating hormone (TSH). Conversely, hyperthyroidism may be treated with optogenetic stabilization of the parvocellular neuroendocrine neurons. For the treatment of adrenal insufficiency, or of Addison's disease, optogenetic excitation of parvocellular neuroendocrine neurons in the supraoptic nucleus and paraventricular nuclei may be used to increase the secretion of vasopressin, which, with the help of corticotropin-releasing hormone (CRH), stimulate anterior pituitary to secrete Adrenocorticotropic hormone (ACTH). Cushing syndrome, frequently caused by excessive ACTH secretion, may be treated with optogenetic stabilization of the parvocellular neuroendocrine neurons of supraoptic nucleus via the same physiological chain of effects described above. Neuroendocrine neurons of the arcuate nucleus produce dopamine, which inhibits secretion of prolactin from the anterior pituitary. Hyperprolactinemia can therefore be treated via optogenetic excitation, while hyperprolactinemia can be treated with optogenetic stabilization of the neuroendocrine cells of the arcuate nucleus.

In the treatment of hyperautonomic states, for example anxiety disorders, optogenetic stabilization of the adrenal medulla may be used to reduce norepinephrine output. Similarly, optogenetic stimulation of the adrenal medulla may be used in persons with need for adrenaline surges, for example those with severe asthma, or disorders that manifest as chronic sleepiness.

Optogenetic stimulation of the adrenal cortex will cause release of chemicals including cortisol, testosterone, and aldosterone. Unlike the adrenal medulla, the adrenal cortex receives its instructions from neuroendocrine hormones secreted from the pituitary and hypothalamus, the lungs, and the kidneys. Regardless, the adrenal cortex is amenable to optogenetic stimulation. Optogenetic stimulation of the cortisol-producing cells of the adrenal cortex may be used to treat Addison's disease. Optogenetic stabilization of cortisol-producing cells of the adrenal cortex may be used to treat Cushing's disease. Optogenetic stimulation of testosterone-producing cells may be used to treat disorders of sexual interest in women: Optogenetic stabilization of those same cells may be used to decrease facial hair in women. Optogenetic stabilization of aldosterone-producing cells within the adrenal cortex may be used to decrease blood pressure. Optogenetic excitation of aldosterone-producing cells within the adrenal cortex may be used to increase blood pressure.

Optogenetic excitation stimulation of specific affected brain regions may be used to increase processing speed, and stimulate growth and interconnection of neurons, including spurring the maturation of neural progenitor cells. Such uses can be particularly useful for treatment of mental retardation.

According to another embodiment of the present invention, various muscle diseases and injuries can be treated. Palsies related to muscle damage, peripheral nerve damage and to dystrophic diseases can be treated with optogenetic excitation to cause contraction, and optogenetic stabilization to cause relaxation. This latter relaxation via optogenetic stabilization approach can also be used to prevent muscle wasting, maintain tone, and permit coordinated movement as opposing muscle groups are contracted. Likewise, frank spasticity can be treated via optogenetic stabilization.

In areas as diverse as peripheral nerve truncation, stroke, traumatic brain injury and spinal cord injury, there is a need to foster the growth of new neurons, and assist with their integration into a functional network with other neurons and with their target tissue. Re-growth of new neuronal tracts may be encouraged via optogenetic excitation, which serves to signal stem cells to sprout axons and dendrites, and to integrate themselves with the network. Use of an optogenetic technique (as opposed to electrodes) prevents receipt of signals by intact tissue, and serves to ensure that new target tissue grows by virtue of a communication set up with the developing neurons, and not with an artificial signal like current emanating from an electrode.

Obesity can be treated with optogenetic excitation to the ventromedial nucleus of the hypothalamus, particularly the proopiomelanocortin (POMC) and cocaine-and-amphetamine-regulating transcript (CART) of the arcuate nucleus.

In an alternative embodiment, obesity can be treated via optogenetic stabilization of the lateral nuclei of the hypothalamus. In another embodiment, optogenetic stimulation to leptin-producing cells, or to cells with leptin receptors within the hypothalamus, may be used to decrease appetite and hence treat obesity.

Destructive lesions to the anterior capsule, and analogous DBS to that region, are established means of treating severe, intractable obsessive-compulsive disorder 48 (OCD48). Such approaches may be emulated using optogenetic stabilization to the anterior limb of the internal capsule, or to regions such as BA32 and Cg24 which show metabolic decrease as OCD remits.

Chronic Pain can be treated using another embodiment of the present invention. Electrical stimulation methods include local peripheral nerve stimulation, local cranial nerve stimulation and "sub-threshold" motor cortex stimulation. Reasonable optogenetic approaches include optogenetic stabilization at local painful sites. Attention to promoter selection would ensure that other sensory and motor fibers would be unaffected. Selective optogenetic excitation of interneurons at the primary motor cortex also may provide effective pain relief. Also, optogenetic stabilization at the sensory thalamus, (particularly medial thalamic nuclei), periventricular grey matter, and ventral raphe nuclei, may be used to produce pain relief. In an alternative embodiment, optogenetic stabilization of parvalbumin-expressing cells targeting as targeting strategy, may be used to treat pain by decreasing Substance P production. The release of endogenous opioids may be accomplished by using optogenetic excitation to increase activity in the nucleus accumbens. In an alternative embodiment, when POMC neurons of the arcuate nucleus of the medial hypothalamus are optogenetically excited, beta endorphin are increased, providing viable treatment approaches for depression and for chronic pain.

Parkinson's Disease can be treated by expressing optogenetic stabilization in the glutamatergic neurons in either the subthalamic nucleus (STN) or the globus pallidus interna (GPi) using an excitatory-specific promoter such as CaMKIIα, and apply optogenetic stabilization. Unlike electrical modulation in which all cell-types are affected, only glutamatergic STN neurons would be suppressed.

Certain personality disorders, including the borderline and antisocial types, demonstrate focal deficits in brain disorders including "hypofrontality." Direct or indirect optogenetic excitation of these regions is anticipated to produce improvement of symptoms. Abnormal bursts of activity in the amygdala are also known to precipitate sudden, unprompted flights into rage: a symptom of borderline personality disorder, as well as other conditions, which can benefit from optogenetic stabilization of the amygdala. Optogenetic approaches could improve communication and synchronization between different parts of the brain, including amygdala, striatum, and frontal cortex, which could help in reducing impulsiveness and improving insight.

The amygdalo-centric model of post-traumatic-stress disorder (PTSD) proposes that it is associated with hyper-arousal of the amygdala and insufficient top-down control by the medial prefrontal cortex and the hippocampus. Accordingly, PTSD may be treated with optogenetic stabilization of the amygdale or hippocampus.

Schizophrenia is characterized by abnormalities including auditory hallucinations. These might be treated by suppression of the auditory cortex using optogenetic stabilization. Hypofrontality associated with schizophrenia might be treated with optogenetic excitation in the affected frontal regions. Optogenetic approaches could improve communication and synchronization between different parts of the brain which could help in reducing misattribution of self-generated stimuli as foreign.

Optogenetic stabilization of cells within the arcuate nucleus of the medial hypothalamus, which contain peptide products of proopiomelanocortin (POMC) and cocaine-and-amphetamine-regulating transcript (CART), can be used to reduce compulsive sexual behavior. Optogenetic excitation of cells within the arcuate nucleus of the medial hypothalamus which contain peptide products of proopiomelanocortin (POMC) and cocaine-and-amphetamine-regulating transcript (CART) may be used to increase sexual interest in the treatment of cases of disorders of sexual desire. In the treatment of disorders of hypoactive sexual desire, testosterone production by the testes and the adrenal glands can be increased through optogenetic excitation of the pituitary gland. Optogenetic excitation of the nucleus accumbens can be used for the treatment of anorgasmia.

The suprachiasmatic nucleus secretes melatonin, which serves to regulate sleep/wake cycles. Optogenetic excitation to the suprachiasmatic nucleus can be used to increase melatonin production, inducing sleep, and thereby treating insomnia. Orexin (hypocretin) neurons strongly excite numerous brain nuclei in order to promote wakefulness. Optogenetic excitation of orexin-producing cell populations can be used to treat narcolepsy, and chronic daytime sleepiness.

Optogenetic stimulation of the supraoptic nucleus may be used to induce secretion of oxytocin, can be used to promote parturition during childbirth, and can be used to treat disorders of social attachment.

Like muscular palsies, the motor functions that have been de-afferented by a spinal cord injury may be treated with optogenetic excitation to cause contraction, and optogenetic stabilization to cause relaxation. This latter relaxation via optogenetic stabilization approach may also be used to prevent muscle wasting, maintain tone, and permit coordinated movement as opposing muscle groups are contracted. Likewise, frank spasticity may be treated via optogenetic stabilization. Re-growth of new spinal neuronal tracts may be encouraged via optogenetic excitation, which serves to signal stem cells to sprout axons and dendrites, and to integrate themselves with the network.

Stroke deficits include personality change, motor deficits, sensory deficits, cognitive loss, and emotional instability. One strategy for the treatment of stroke deficits is to provide optogenetic stimulation to brain and body structures that have been deafferented from excitatory connections. Similarly, optogenetic stabilization capabilities can be imparted on brain and body structures that have been deafferented from inhibitory connections.

Research indicates that the underlying pathobiology in Tourette's syndrome is a phasic dysfunction of dopamine transmission in cortical and subcortical regions, the thalamus, basal ganglia and frontal cortex. In order to provide therapy, affected areas are preferably first identified using techniques including functional brain imaging and magnetoencephalography (MEG). Whether specifically identified or not, optogenetic stabilization of candidate tracts may be used to suppress motor tics. Post-implantation empirical testing of device parameters reveals which sites of optogenetic stabilization, and which are unnecessary to continue.

In order to treat disorders of urinary or fecal incontinence optogenetic stabilization can be used to the sphincters, for example via optogenetic stabilization of the bladder detrussor smooth muscle or innervations of that muscle. When micturation is necessary, these optogenetic processes are turned off, or alternatively can be reversed, with optogenetic stabilization to the (external) urinary sphincter, and optogenetic excitation of the bladder detrussor muscle or its innervations. When a bladder has been deafferentated, for example, when the sacral dorsal roots are cut or destroyed by diseases of the dorsal roots such as tabes dorsalis in humans, all reflex contractions of the bladder are abolished, and the bladder becomes distended. Optogenetic excitation of the muscle directly can be used to restore tone to the detrussor, prevent kidney damage, and to assist with the micturition process. As the bladder becomes "decentralized" and hypersensitive to movement, and hence prone to incontinence, optogenetic stabilization to the bladder muscle can be used to minimize this reactivity of the organ.

In order to selectively excite/inhibit a given population of neurons, for example those involved in the disease state of an illness, several strategies can be used to target the optogenetic proteins/molecules to specific populations.

For various embodiments of the present invention, genetic targeting may be used to express various optogenetic proteins or molecules. Such targeting involves the targeted expression of the optogenetic proteins/molecules via genetic control elements such as promoters (e.g., Parvalbumin, Somatostatin, Cholecystokinin, GFAP), enhancers/silencers (e.g., Cytomegalovirus Immediate Early Enhancer), and other transcriptional or translational regulatory elements (e.g., Woodchuck Hepatitis Virus Post-transcriptional Regulatory Element). Permutations of the promoter+enhancer+regulatory element combination can be used to restrict the expression of optogenetic probes to genetically-defined populations.

Various embodiments of the present invention may be implemented using spatial/anatomical targeting. Such targeting takes advantage of the fact that projection patterns of neurons, virus or other reagents carrying genetic information (DNA plasmids, fragments, etc.), can be focally delivered to an area where a given population of neurons project to. The genetic material will then be transported back to the bodies of the neurons to mediate expression of the optogenetic probes. Alternatively, if it is desired to label cells in a focal region, viruses or genetic material may be focally delivered to the interested region to mediate localized expression.

Various gene delivery systems are useful in implementing one or more embodiments of the present invention. One such delivery system is Adeno-Associated Virus (AAV). AAV can be used to deliver a promoter+optogenetic probe cassette to a specific region of interest. The choice of promoter will drive expression in a specific population of neurons. For example, using the CaMKIIα promoter will drive excitatory neuron specific expression of optogenetic probes. AAV will mediate long-term expression of the optogenetic probe for at least 1 year or more. To achieve more specificity, AAV may be pseudo-typed with specific serotypes 1 to 8, with each having different trophism for different cell types. For instance, serotype 2 and 5 is known to have good neuron-specific trophism.

Another gene delivery mechanism is the use of a retrovirus. HIV or other lentivirus-based retroviral vectors may be used to deliver a promoter+optogenetic probe cassette to a specific region of interest. Retroviruses may also be pseudotyped with the Rabies virus envelope glycoprotein to achieve retrograde transport for labeling cells based on their axonal projection patterns. Retroviruses integrate into the host cell's genome, therefore are capable of mediating permanent expression of the optogenetic probes. Non-lentivirus based retroviral vectors can be used to selectively label dividing cells.

Gutless Adenovirus and Herpes Simplex Virus (HSV) are two DNA based viruses that can be used to deliver promoter+optogenetic probe cassette into specific regions of the brain as well. HSV and Adenovirus have much larger packaging capacities and therefore can accommodate much larger promoter elements and can also be used to deliver multiple optogenetic probes or other therapeutic genes along with optogenetic probes.

Focal Electroporation can also be used to transiently transfect neurons. DNA plasmids or fragments can be focally delivered into a specific region of the brain. By applying mild electrical current, surrounding local cells will receive the DNA material and expression of the optogenetic probes.

In another instance, lipofection can be used by mixing genetic material with lipid reagents and then subsequently injected into the brain to mediate transfect of the local cells.

Various embodiments involve the use of various control elements. In addition to genetic control elements, other control elements (particularly promoters and enhancers whose activities are sensitive to chemical, magnetic stimulation or infrared radiation) can be used to mediate temporally-controlled expression of the optogenetic probes. For example, a promoter whose transcriptional activity is subject to infrared radiation allows one to use focused radiation to fine tune the expression of optogenetic probes in a focal region at only the desired time.

According to one embodiment of the present invention, the invention may be used in animal models of DBS, for example in Parkinsonian rats, to identify the target cell types responsible for therapeutic effects (an area of intense debate and immense clinical importance). For instance, stimulation can be targeted to specific/small neural populations within larger populations known to provide therapeutic effects in response to stimulus. These targeted populations can then be stimulated to quantify the source of the therapeutic effects. The targeting can be implemented using spatially controlled application of the proteins within the brain and/or by tailoring the proteins for expression in specific neural cell types. The targeting can also be implemented by controlling the light delivery in terms of spatial location, wavelength, intensity and/or temporal stimulation properties. Knowledge gained from such characterization can then be used in the development of pharmacological and surgical strategies for treating human disease. Such modeling and characterization is not limited to Parkinson's and can be applied to a vast array of disease and circuit modeling.

According to another embodiment of the present invention, genetically-defined cell types may be linked with complex systems-level behaviors, to allow the elucidation of the precise contribution of different cell types in many different brain regions to high-level organismal functioning.

Other aspects and embodiments are directed to systems, methods, kits, compositions of matter and molecules for ion pumps or for controlling inhibitory currents in a cell (e.g., for in vivo and in vitro environments). As described throughout this disclosure, including the claims, such systems, methods, kits, compositions of matter are realized in manners consistent herewith. For example, in one embodiment, the present invention is directed to an assembly or kit of parts, having a product containing an NpHR-based molecular variant and another opsin-based molecule (SFO/VChR1/ChR2-based and or NpHR-based) as a combined preparation for use in the treatment of disease of a neurological or CNS disorder (as a category of disorder types or a specific disorder as exemplified herein), wherein at least the NpHR-based molecular variant is useful for expressing a light-activated NpHR-based molecule that responds to light by producing an inhibitory current to dissuade depolarization of a cell, and wherein a high expression of the molecule manifests a toxicity level that is less than about 75% (e.g., one or more of Seq Id Nos. 4-13).

Embodiments of the present invention employ implantable arrangements for in vivo use. These arrangements can include a light generator, such as a light-emitting diode, laser or similar light source and a biological portion that modifies target cells to facilitate stimulation of the target cells in response to light generated by the light generator.

In one embodiment of the present invention, a biological portion may be composed of target cells that have been modified to be photosensitive. In another embodiment of the present invention, a biological portion may contain biological elements such as gene transfer vectors, which cause target cells to become sensitive to light. An example of this is lentiviruses carrying the gene for SFO (ChR2/VChR1 mutants) expression. In this manner, the stimulation of target cells can be controlled by an implantable device. For example, a control circuit can be arranged to respond to an external signal by activating, or deactivating a light source, or by charging a battery that powers light source. In one instance, the external signal is electromagnetic radiation that is received by a control circuit. For example, radio frequency (RF) signals can be transmitted by an external RF transmitter and received by a control circuit. In another example, a magnetic field can be used to activate and/or power the control circuit.

Control circuits can be implemented using varying degrees of complexity. In one instance, the circuit is a simple coil that when exposed to a magnetic field generates a current. The current is then used to power a light source. Such an implementation can be particularly useful for limiting the size and complexity as well as increasing the longevity of the device. In another instance, a control circuit can include an RF antenna. Optionally, a battery or similar power source, such as a capacitive element, can be used by the control circuit. While charged, the power source allows the circuitry to continue to operate without need for concurrent energy delivery from outside the body. This can be particularly useful for providing precise control over the light emitted by a light source and for increased intensity of the emitted light.

In one embodiment of the present invention, a light source is implemented using a light-emitting-diode (LED). LEDs have been proven to be useful for low power applications and also to have a relatively fast response to electrical signals.

In another embodiment of the present invention, the biological portion includes a gelatin or similar substance that contains gene transfer vectors which genetically code the target cells for photosensitivity. In one instance, the vectors are released once implanted into the body. This can be accomplished, for example, by using a containment material that allows the vectors to be released into aqueous solution (e.g., using dehydrated or water soluble materials such as gelatins). The release of the vectors results in the target cells being modified such that they are simulated in response to light from a light source.

In another embodiment of the present invention, the biological portion includes a synthetic mesh that contains the photosensitive cells. In one instance, the cells are neurons that have been modified to be photosensitive. The synthetic mesh can be constructed so as to allow the dendrites and axons to pass through the mess without allowing the entire neuron (e.g., the cell body) to pass. One example of such a mesh has pores that are on the order of 3-7 microns in diameter and is made from polyethylene terephthalate. In another example embodiment, the biological portion includes an injection mechanism for targeted delivery.

In various implementations, a system is adapted such that the delivery device introduces the light responsive protein by one of transfection, transduction or microinjection, and/ or such that the light source introduces light to an SFO expressing neuron via one of an implantable light generator and fiber-optics.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include additional modifications other than those listed herein. Such modifications and changes do not depart from the true spirit and scope of the present invention, which is set forth in the following appended claims.

What is claimed is:

1. A light-responsive ion channel comprising an amino acid sequence having at least 90% amino acid sequence identity to the amino acid sequence set forth in SEQ ID NO:2, wherein the ion channel exhibits an extended conducting state after exposure to a light pulse, and wherein the ion channel comprises: i) a substitution of a cysteine residue at a position corresponding to amino acid residue 123 (C123) of SEQ ID NO:2 with a serine; and ii) a substitution of an aspartic acid residue at a position corresponding to amino acid residue 151 (D151) of SEQ ID NO:2 with an alanine.

2. The light-responsive ion channel of claim 1, wherein the light-responsive ion channel comprises an amino acid sequence having at least 95% amino acid sequence identity to the amino acid sequence set forth in SEQ ID NO:2.

3. A nucleic acid comprising a nucleotide sequence encoding the light-responsive ion channel of claim 1.

4. The nucleic acid of claim 3, wherein the nucleic acid is an expression vector.

5. The nucleic acid of claim 4, wherein the expression vector is a lentivirus vector.

6. The nucleic acid of claim 4, wherein the expression vector is an adeno-associated virus vector.

7. The nucleic acid of claim 4, wherein the expression vector is an adenovirus-based vector.

8. The nucleic acid of claim 3, wherein the nucleotide sequence is operably linked to a control element.

9. The nucleic acid of claim 8, wherein the control element is a promoter.

10. The nucleic acid of claim 9, wherein the promoter is a CaMKIIα promoter.

11. The nucleic acid of claim 4, wherein the expression vector is a herpes simplex virus-based vector.

* * * * *